US010130665B2

(12) United States Patent
Lawley et al.

(10) Patent No.: US 10,130,665 B2
(45) Date of Patent: Nov. 20, 2018

(54) METHOD FOR IDENTIFYING BACTERIA FOR BACTERIOTHERAPY

(71) Applicant: GENOME RESEARCH LIMITED, London (GB)

(72) Inventors: Trevor D. Lawley, London (GB); Simon Clare, London (GB); Gordon Dougan, London (GB)

(73) Assignee: GENOME RESEARCH LIMITED, London (GB)

( * ) Notice: Subject to any disclaimer, the term of this patent is extended or adjusted under 35 U.S.C. 154(b) by 378 days.

(21) Appl. No.: 14/402,033

(22) PCT Filed: May 20, 2013

(86) PCT No.: PCT/GB2013/051298
§ 371 (c)(1),
(2) Date: Nov. 18, 2014

(87) PCT Pub. No.: WO2013/171515
PCT Pub. Date: Nov. 21, 2013

(65) Prior Publication Data
US 2016/0022746 A1   Jan. 28, 2016

(30) Foreign Application Priority Data

May 18, 2012  (GB) .................................. 1208845.6
Jul. 5, 2012  (GB) .................................. 1211961.6

(51) Int. Cl.
*C12Q 1/04* (2006.01)
*A61K 35/741* (2015.01)
(Continued)

(52) U.S. Cl.
CPC ............ *A61K 35/747* (2013.01); *A61K 35/74* (2013.01); *A61K 35/744* (2013.01); *C12Q 1/04* (2013.01); *C12Q 1/689* (2013.01)

(58) Field of Classification Search
None
See application file for complete search history.

(56) References Cited

U.S. PATENT DOCUMENTS

2007/0196890 A1* 8/2007 Vulevic .................. C12Q 1/025
                                                                  435/34
2009/0022849 A1* 1/2009 Clifford .................... A23L 2/84
                                                                  426/61

FOREIGN PATENT DOCUMENTS

WO    WO 97/09886        3/1997
WO    WO 02/07741 A1     1/2002
(Continued)

OTHER PUBLICATIONS

Tvede, M; Rask-Madsen, J "Bacteriotherapy for Chronic Relapsing Clostridium difficile Diarrhoea in Six Patients" Lancet, May 27, 1989, 333(8648), p. 1156-1160. doi:10.1016/S0140-6736(89)92749-9.*

(Continued)

*Primary Examiner* — Robert J Yamasaki
*Assistant Examiner* — Charles Zoltan Constantine
(74) *Attorney, Agent, or Firm* — Cooley LLP

(57) ABSTRACT

A method, for the identification of bacterial isolates suitable for use in bacteriotherapy, the method comprising: (i) preparing a suspension of material collected from a host harboring microbiota; (ii) addition of an activator of bacterial spores sufficient to allow growth of bacteria from spores present in the suspension; (iii) culturing the suspension; and (iv) identification of at least one bacterial species within the culture.

15 Claims, 14 Drawing Sheets
Specification includes a Sequence Listing.

(51) Int. Cl.
    *A61K 35/74*     (2015.01)
    *A61K 35/747*     (2015.01)
    *A61K 35/744*     (2015.01)
    *C12Q 1/689*     (2018.01)

(56) References Cited

FOREIGN PATENT DOCUMENTS

| WO | WO 2011/033310 A1 | 3/2011 |
| WO | WO 2011/094027 | 9/2011 |
| WO | WO 2013/053836 A1 | 4/2013 |

OTHER PUBLICATIONS

Goodman, "Extensive personal human gut microbiota culture collections characterized and manipulated in gnotobiotic mice" PNAS, 2011, vol. 108, No. 15 6252-6257. (Year: 2011).*

Bakken Johan S: "Fecal Bacteriotherapy for Recurrent Clostridium difficile infection", Anaerobe, vol. 15, No. 6, Jan. 1, 2009.

Trevor D. Lawley et al: "Targeted Restoration of the Intestinal Microbiota with a Simple, Defined Bacteriotherapy Resolves Relapsing Clostridium difficile Disease in Mice", PLOS Pathogens, vol. 8, No. 10, Oct. 25, 2012.

Tvede M et al: "Bacteriotherapy for Chronic Relapsing Clostridium Difficile Diarrhoea in Six Patients", The Lancet, Lancet Limited. London, GB, vol. 1, No. 8648, May 27, 1989.

* cited by examiner

Figure 1
Figure 1a)
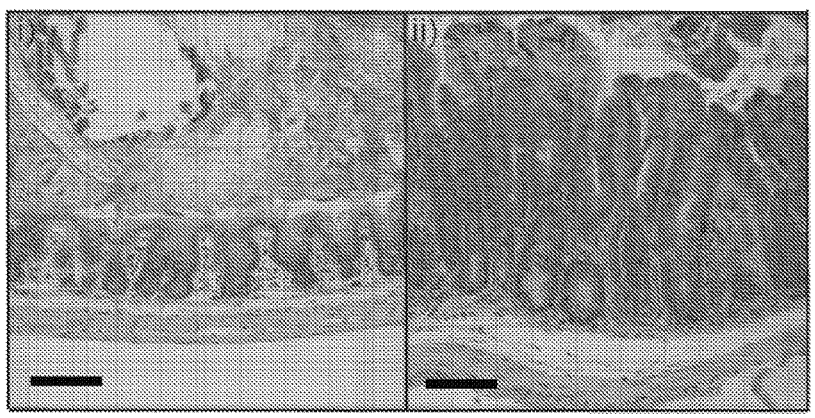
Figure 1b)
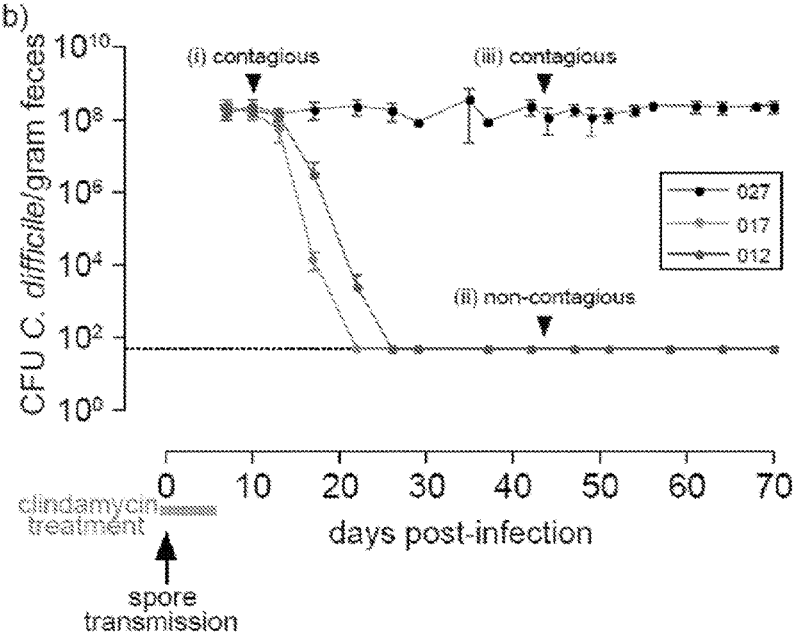

Figure 2
Figure 2 a)
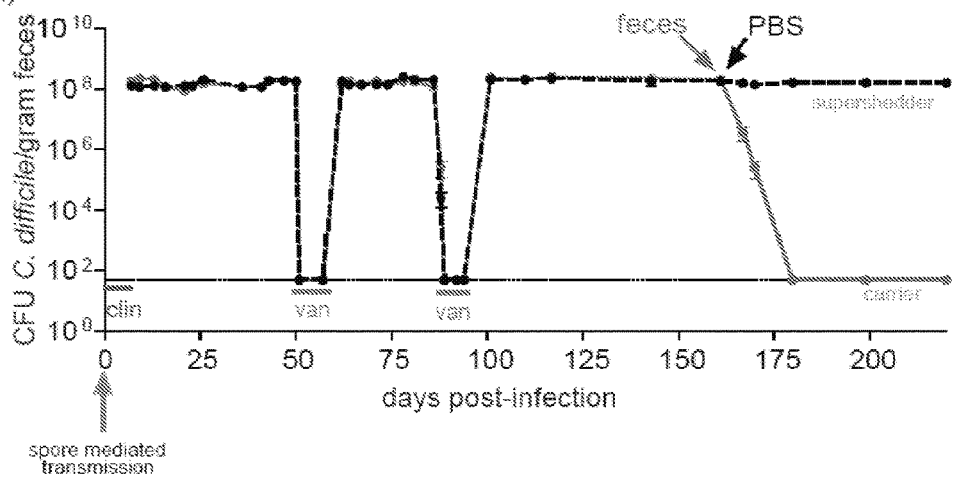
Figure 2b)
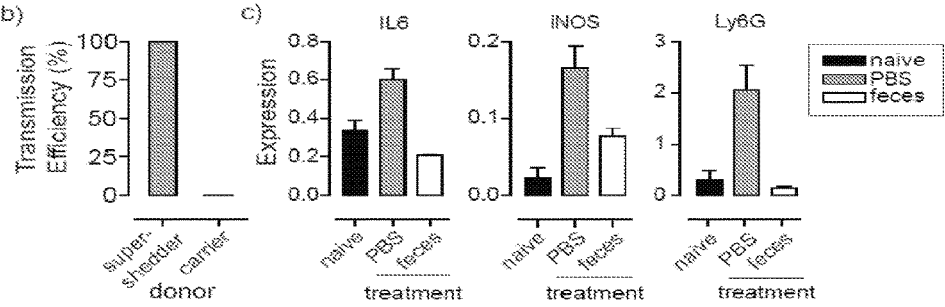

Figure 13
Fig. 13 a)
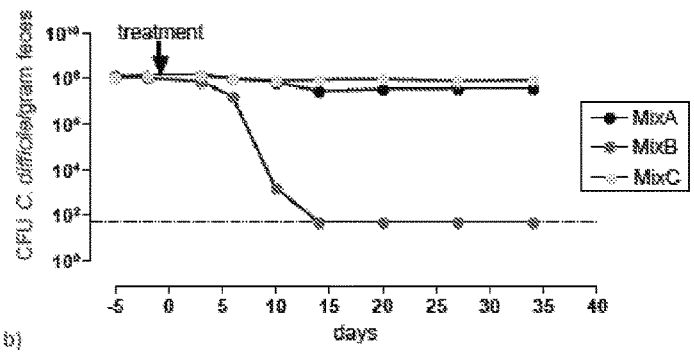
Fig. 13 b)
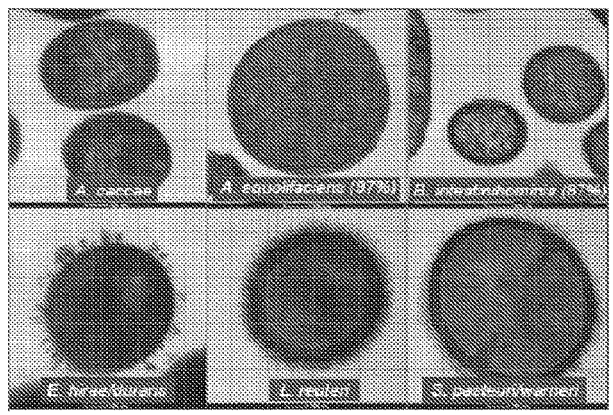
Fig. 13 c)
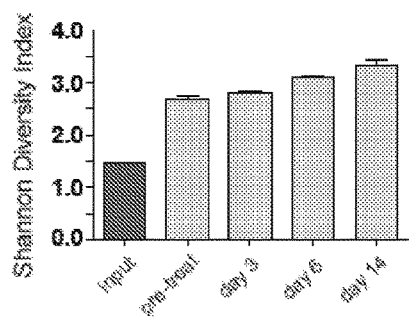

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Gapdh PCR primer

<400> SEQUENCE: 1
tgtgtccgtc gtggatctga                                       20

<210> SEQ ID NO 2
<211> LENGTH: 25
<212> TYPE: DNA
<213> ORGANISM: Artificial Sequence
<220> FEATURE:
<223> OTHER INFORMATION: Gapdh PCR primer

<400> SEQUENCE: 2
caccaccttc ttgatgtcat catac                                 25
```

<210> SEQ ID NO 3
<211> LENGTH: 21
<212> TYPE: DNA
<213> ORGANISM: Artificial Sequence
<220> FEATURE:
<223> OTHER INFORMATION: Gapdh probe

<400> SEQUENCE: 3
tgccgcctgg agaaacctgc c                                              21

<210> SEQ ID NO 4
<211> LENGTH: 25
<212> TYPE: DNA
<213> ORGANISM: Artificial Sequence
<220> FEATURE:
<223> OTHER INFORMATION: IL-6 PCR primer

<400> SEQUENCE: 4
acaagtcgga ggcttaatta cacat                                          25

<210> SEQ ID NO 5
<211> LENGTH: 22
<212> TYPE: DNA
<213> ORGANISM: Artificial Sequence
<220> FEATURE:
<223> OTHER INFORMATION: IL-6 PCR primer

<400> SEQUENCE: 5
ttgccattgc acaactcttt tc                                             22

<210> SEQ ID NO 6
<211> LENGTH: 23
<212> TYPE: DNA
<213> ORGANISM: Artificial Sequence
<220> FEATURE:
<223> OTHER INFORMATION: IL-6 probe

<400> SEQUENCE: 6
ttctctggga aatcgtggaa atg                                            23

<210> SEQ ID NO 7
<211> LENGTH: 17
<212> TYPE: DNA
<213> ORGANISM: Artificial Sequence
<220> FEATURE:
<223> OTHER INFORMATION: iNOS PCR primer

<400> SEQUENCE: 7
tgcatcggca ggatcca                                                   17

<210> SEQ ID NO 8
<211> LENGTH: 23
<212> TYPE: DNA
<213> ORGANISM: Artificial Sequence
<220> FEATURE:
<223> OTHER INFORMATION: iNOS PCR primer

<400> SEQUENCE: 8
aacatttcct gtgctgtgct aca                                            23

<210> SEQ ID NO 9
<211> LENGTH: 24
<212> TYPE: DNA
<213> ORGANISM: Artificial Sequence
<220> FEATURE:

<223> OTHER INFORMATION: iNOS probe

<400> SEQUENCE: 9
cctgcaggtc tttgacgctc ggaa                                           24

<210> SEQ ID NO 10
<211> LENGTH: 20
<212> TYPE: DNA
<213> ORGANISM: Artificial Sequence
<220> FEATURE:
<223> OTHER INFORMATION: Ly6G PCR primer

<400> SEQUENCE: 10
tgccccttct ctgatggatt                                                20

<210> SEQ ID NO 11
<211> LENGTH: 23
<212> TYPE: DNA
<213> ORGANISM: Artificial Sequence
<220> FEATURE:
<223> OTHER INFORMATION: Ly6G PCR primer

<400> SEQUENCE: 11
tgctcttgac tttgcttctg tga                                            23

<210> SEQ ID NO 12
<211> LENGTH: 34
<212> TYPE: DNA
<213> ORGANISM: Artificial Sequence
<220> FEATURE:
<223> OTHER INFORMATION: Ly6G probe

<400> SEQUENCE: 12
tgcgttgctc tggagataga agttattgtg gact                                34

<210> SEQ ID NO 13
<211> LENGTH: 1318
<212> TYPE: DNA
<213> ORGANISM: Unknown
<220> FEATURE:
<223> OTHER INFORMATION: 97% identity to Adlercreutzia equolifaciens 16S
      rRNA

<400> SEQUENCE: 13
acgggtgagt aacacgtgac caacctgccc cgcgctccgg gacaccgctg gaaacggcgg    60
ctaataccgg atactccggg agggccccat ggccctgccg ggaaagccga cgggcgcgg    120 gatgggtcg cggcccatta ggtagacggc ggggtaacgg cccaccgtgc ccgcgatggg    180
tagccggact gagaggtcga ccggccacat ggggactgag atacggccca gactcctacg    240
ggaggcagca gtgggaatt ttgcgcaatg gggggaaccc tgacgcagca acgccgcgtg     300
cgggacgaag gccctcgggt tgtaaaccgc tttcagcagg gaagatccaa gacggtacct    360
gcagaagaag ctccggctaa ctacgtgcca gcagccgcgg taatacgtag ggggcgagcg    420
ttatccggat tcattgggcg taaagcgcgc gtaggcggcc gcctaagcgg gacctctaac    480
cccggggctc aaccccgggc cgggtcccgg actgggcggc tcgagtgcgg tagaggagag    540
cggaattccc ggtgtagcgg tggaatgcgc agatatcggg aagaacaccg atggcgaagg    600
cagctctctg ggccgtcact gacgctgagg cgcgaaagct gggggagcga acaggattag    660 atacctggt agtcccagcc gtaaacgatg gcgctaggt gtggggggac gatccctccg     720
tgccgcagcc aacgcattaa gcgccccgcc tggggagtac ggccgcaagg ctaaaactca    780

-continued

```
aaggaattga cggggccccg cacaagcagc ggagcatgtg gcttaattcg aagcaacgcg      840
aagaacctta ccagggcttg acatgccgat gaagccgggg agaccggtg gccgagagga       900 gtcggcgcag gtggtgcatg gctgtcgtca gctcgtgtcg tgagatgttg ggttaagtcc     960
cgcaacgagc gcaaccccg ccccgtgttg ccagcattca gttggggact cgcgggggac     1020
tgccggcgtc aagccggagg aaggtgggga cgacgtcaag tcatcatgcc ccttatgccc    1080
tgggctgcac acgtgctaca atggccggta cagagggttg ccaccccgcg aggggagcg     1140 gatcccggaa agccggtccc agttcggatc gcaggctgca acccgcctgc gtgaagccgg    1200
agttgctagt aatcgcggat cagcacgccg cggtgaatac gttcccgggc cttgtacaca    1260
ccgcccgtca caccaccga gtcgtctgca cccgaagccg ccggccgaac ccccgggg      1318
```

<210> SEQ ID NO 14
<211> LENGTH: 1292
<212> TYPE: DNA
<213> ORGANISM: Unknown
<220> FEATURE:
<223> OTHER INFORMATION: 98% identity to Anaerostipes caccae 16S rRNA

<400> SEQUENCE: 14

```
agtggcggac gggtgagtaa cgcgtgggga acctgcccta tacaggggga taacagctgg     60
aaacggctgc taataccgca taagcgcaca gaatcgcatg attcggtgtg aaaagctccg    120
gcagtatagg atggtcccgc gtctgattag ctggttggcg gggtaacggc ccaccaaggc    180
gacgatcagt agccggcttg agagagtgga cggccacatt gggactgaga cacggcccaa    240
actcctacgg gaggcagcag tggggaatat tgcacaatgg gggaaaccct gatgcagcga    300
cgccgcgtga gtgaagaagt atttcggtat gtaaagctct atcagcaggg aagaaaaaag    360
acggtacctg actaagaagc cccggctaac tacgtgccag cagccgcggt aatacgtagg    420
gggcaagcgt tatccggaat tactgggtgt aaagggtgcg taggtggcat ggtaagtcag    480
aagtgaaagc ccggggctta acccgggac tgcttttgaa actgtcatgc tggagtgcag    540
gagaggtaag cggaattcct agtgtagcgg tgaaatgcgt agatattagg aggaacacca    600
gtggcgaagg cggcttactg gactgtcact gacactgatg cacgaaagcg tggggagcaa    660
acaggattag ataccctggt agtccacgcc gtaaacgatg aatactaggt gtcggggccg    720
tagaggcttc ggtgccgcag caaacgcagt aagtattcca cctggggagt acgttcgcaa    780
gaatgaaact caaaggaatt gacggggacc cgcacaagcg gtggagcatg tggtttaatt    840
cgaagcaacg cgaagaacct tacctggtct tgacatctaa ctgaccggtt cgtaatggga    900
cctttccttc gggacagtta agacaggtgg tgcatggttg tcgtcagctc gtgtcgtgag    960
atgttgggtt aagtcccgca acgagcgcaa ccccatctt tagtagccag catataaggt   1020
gggcactcta gagagactgc cagggataac ctggaggaag gtggggacga cgtcaaatca   1080
tcatgcccct tatggccagg gctacacacg tgctacaatg gcgtaaacaa agggaagcga   1140
agtcgtgagg cgaagcaaat cccagaaata acgtctcagt tcggattgta gtctgcaact   1200
cgactacatg aagctggaat cgctagtaat cgtgaatcag aatgtcacgg tgaatacgtt   1260
cccgggtctt gtacacaccg cccgtcacac ca                                 1292
```

<210> SEQ ID NO 15
<211> LENGTH: 1324
<212> TYPE: DNA
<213> ORGANISM: Staphylococcus warneri

<400> SEQUENCE: 15

```
agcggcggac gggtgagtaa cacgtggata acctacctat aagactggga taacttcggg      60
aaaccggagc taataccgga taacatattg aaccgcatgg ttcaatagtg aaaggcggct     120
ttgctgtcac ttatagatgg atccgcgccg tattagctag ttggtaaggt aacggcttac     180
caaggcaacg atacgtagcc gacctgagag ggtgatcggc cacactggaa ctgagacacg     240
gtccagactc ctacgggagg cagcagtagg gaatcttccg caatgggcga agcctgacg      300 gagcaacgcc gcgtgagtga tgaaggtctt cggatcgtaa aactctgtta tcagggaaga     360
acaaatgtgt aagtaactgt gcacatcttg acggtacctg atcagaaagc cacggctaac     420
tacgtgccag cagccgcggt aatacgtagg tggcaagcgt tatccggaat tattgggcgt     480
aaagcgcgcg taggcggttt tttaagtctg atgtgaaagc ccacggctca accgtggagg     540
gtcattggaa actggaaaac ttgagtgcag aagaggaaag tggaattcca tgtgtagcgg     600
tgaaatgcgc agagatatgg aggaacacca gtggcgaagg cgactttctg gtctgtaact     660
gacgctgatg tgcgaaagcg tggggatcaa acaggattag ataccctggt agtccacgcc     720
gtaaacgatg agtgctaagt gttaggggt ttccgcccct tagtgctgca gctaacgcat     780
taagcactcc gcctggggag tacgaccgca aggttgaaac tcaaaggaat tgacggggac     840
ccgcacaagc ggtggagcat gtggtttaat tcgaagcaac gcgaagaacc ttaccaaatc     900
ttgacatcct ttgaccgctc tagagataga gtcttcccct tcggggggaca aagtgacagg     960 tggtgcatgg ttgtcgtcag ctcgtgtcgt gagatgttgg gttaagtccc gcaacgagcg    1020 caaccettaa gcttagttgc catcattaag ttgggcactc taagttgact gccggtgaca    1080
aaccggagga aggtggggat gacgtcaaat catcatgccc cttatgattt gggctacaca    1140
cgtgctacaa tggacaatac aaagggcagc taaaccgcga ggtcaagcaa atcccataaa    1200
gttgttctca gttcggattg tagtctgcaa ctcgactaca tgaagctgga atcgctagta    1260
atcgtagatc agcatgctac ggtgaatacg ttcccgggtc ttgtacacac cgcccgtcac    1320
acca                                                                 1324
```

<210> SEQ ID NO 16
<211> LENGTH: 1323
<212> TYPE: DNA
<213> ORGANISM: Lactobacillus reuteri

<400> SEQUENCE: 16

```
agtggcggac gggtgagtaa cacgtaggta acctgccccg gagcggggga taacatttgg      60
aaacagatgc taataccgca taacaacaaa agccacatgg cttttgtttg aaagatggct     120
ttggctatca ctctgggatg gacctgcggt gcattagcta gttggtaagg taacggctta     180
ccaaggcgat gatgcatagc cgagttgaga gactgatcgg ccacaatgga actgagacac     240
ggtccatact cctacgggag gcagcagtag ggaatcttcc acaatgggcg caagcctgat     300
ggagcaacac cgcgtgagtg aagaagggtt tcggctcgta aagctctgtt gttggagaag     360
aacgtgcgtg agagtaactg ttcacgcagt gacggtatcc aaccagaaag tcacggctaa     420
ctacgtgcca gcagccgcgg taatacgtag gtggcaagcg ttatccggat ttattgggcg     480
taaagcgagc gcaggcggtt gcttaggtct gatgtgaaag ccttcggctt aaccgaagaa     540
gtgcatcgga aaccgggcga cttgagtgca gaagaggaca gtggaactcc atgtgtagcg     600
gtggaatgcg tagatatatg gaagaacacc agtggcgaag gcggctgtct ggtctgcaac     660
tgacgctgag gctcgaaagc atgggtagcg aacaggatta gataccctgg tagtccatgc     720
```

| | |
|---|---:|
| cgtaaacgat gagtgctagg tgttggaggg tttccgccct tcagtgccgg agctaacgca | 780 |
| ttaagcactc cgcctgggga gtacgaccgc aaggttgaaa ctcaaaggaa ttgacggggg | 840 |
| cccgcacaag cggtggagca tgtggtttaa ttcgaagcta cgcgaagaac cttaccaggt | 900 |
| cttgacatct tgcgctaacc ttagagataa ggcgttccct tcggggacgc aatgacaggt | 960 |
| ggtgcatggt cgtcgtcagc tcgtgtcgtg agatgttggg ttaagtcccg caacgagcgc | 1020 |
| aaccCttgtt actagttgcc agcattaagt tgggcactct agtgagactg ccggtgacaa | 1080 |
| accggaggaa ggtggggacg acgtcagatc atcatgcccc ttatgacctg gctacacac | 1140 |
| gtgctacaat ggacggtaca acgagtcgca agctcgcgag agtaagctaa tctcttaaag | 1200 |
| ccgttctcag ttcggactgt aggctgcaac tcgcctacac gaagtcggaa tcgctagtaa | 1260 |
| tcgcggatca gcatgccgcg gtgaatacgt tcccgggcct tgtacacacc gcccgtcaca | 1320 |
| cca | 1323 |

<210> SEQ ID NO 17
<211> LENGTH: 1323
<212> TYPE: DNA
<213> ORGANISM: Enterococcus hirae

<400> SEQUENCE: 17

| | |
|---|---:|
| agtggcgaac gggtgagtaa cacgtgggta acctgcccat cagaagggga taacacttgg | 60 |
| aaacaggtgc taataccgta taacaatcga accgcatgg tttcgatttg aaaggcgctt | 120 |
| tcgggtgtcg ctgatggatg acccgcggt gcattagcta gttggtgagg taacggctca | 180 |
| ccaaggcgac gatgcatagc cgacctgaga gggtgatcgg ccacattggg actgagacac | 240 |
| ggcccaaact cctacgggag gcagcagtag ggaatcttcg gcaatggacg aaagtctgac | 300 |
| cgagcaacgc cgcgtgagtg aagaaggttt tcggatcgta aaactctgtt gttagagaag | 360 |
| aacaaggatg agagtaactg ttcatccctt gacggtatct aaccagaaag ccacggctaa | 420 |
| ctacgtgcca gcagccgcgg taatacgtag gtggcaagcg ttgtccggat ttattgggcg | 480 |
| taaagcgagc gcaggcggtt tcttaagtct gatgtgaaag ccccggctc aaccggggag | 540 |
| ggtcattgga aactgggaga cttgagtgca gaagaggaga gtggaattcc atgtgtagcg | 600 |
| gtgaaatgcg tagatatatg gaggaacacc agtggcgaag gcggctctct ggtctgtaac | 660 |
| tgacgctgag gctcgaaagc gtggggagca acaggatta gataccctgg tagtccacgc | 720 |
| cgtaaacgat gagtgctaag tgttggaggg tttccgccct tcagtgctgc agctaacgca | 780 |
| ttaagcactc cgcctgggga gtacgaccgc aaggttgaaa ctcaaaggaa ttgacggggg | 840 |
| cccgcacaag cggtggagca tgtggtttaa ttcgaagcaa cgcgaagaac cttaccaggt | 900 |
| cttgacatcc tttgaccact ctagagatag agcttcccct tcgggggcaa agtgacaggt | 960 |
| ggtgcatggt tgtcgtcagc tcgtgtcgtg agatgttggg ttaagtcccg caacgagcgc | 1020 |
| aaccCttatt gttagttgcc atcattcagt tgggcactct agcaagactg ccggtgacaa | 1080 |
| accggaggaa ggtggggatg acgtcaaatc atcatgcccc ttatgacctg gctacacac | 1140 |
| gtgctacaat gggaagtaca acgagtcgca aagtcgcgag gctaagctaa tctcttaaag | 1200 |
| cttctctcag ttcggattgt aggctgcaac tcgcctacat gaagccggaa tcgctagtaa | 1260 |
| tcgcggatca gcacgccgcg gtgaatacgt tcccgggcct tgtacacacc gcccgtcaca | 1320 |
| cca | 1323 |

<210> SEQ ID NO 18
<211> LENGTH: 1308

<212> TYPE: DNA
<213> ORGANISM: Unknown
<220> FEATURE:
<223> OTHER INFORMATION: 87% identity to Barnesiella intestinihominis 16S rRNA

<400> SEQUENCE: 18

```
accggcgcac gggtgagtaa cacgtatgca acctgccctc ttcagggga caaccttccg      60 aaagggaggc taatcccgcg tatatcggtt tcgggcatcc gttatcgagg aaagattcat     120
cggaagagga tgggcatgcg gcgcattagc ttgacggcgg ggtaacggcc caccgtggcg    180
acgatgcgta ggggttctga gaggaaggtc ccccacactg gtactgagac acggaccaga    240
ctcctacggg aggcagcagt gaggaatatt ggtcaatggg agagatcctg aaccagccaa    300
gccgcgtgag ggaagacggc cctatggggtt gtaaacctct tttgtcggag aacaaaaccc   360
gggacgagtc ccggactgcg tgtatccgaa gaaaaagcat cggctaactc cgtgccagca    420
gccgcggtaa tacggaggat gcgagcgtta tccggattta ttgggtttaa agggtgcgta    480
ggcggtccgt taagtcagcg gtaaaattgc ggggctcaac cccgtcgagc cgttgaaact    540
ggcagacttg agttggcgag aagtacgcgg aatgcgcggt gtagcggtga aatgcataga    600
tatcgcgcag aactccgatt gcgaaggcag cgtaccggcg ccagactgac gctgaggcac    660
gaaagcgtgg ggatcgaaca ggattagata ccctggtagt ccacgcagta aacgatgaat    720
gctaggtgtc cgggtcgaat gagacctggg cggcgaagcg aaagcgataa gcattccacc    780
tggggagtac gccggcaacg gtgaaactca aaggaattga cggggcccg cacaagcgga     840 ggaacatgtg gtttaattcg atgatacgcg aggaaccta cccgggctca acgggagtg      900 gaatggacca gagacggttc agcctacggg ccgcttccga ggtgctgcat ggttgtcgtc    960
agctcgtgcc gtgaggtgtc ggcttaagtg ccataacgag cgcaacccc gccggcagtt   1020 gctaacgggc aatgccgagg actctgccgg gactgccgcc gcaaggcgtg aggaaggcgg   1080
ggatgacgtc aaatcagcac ggcccttacg tccggggcga cacacgtgtt acaatgggcg   1140
gtacagcggg aagccaggcg gcgacgccga gcggaacccg aaagccgttc tcagttcgga   1200
tcggagtctg caacccgact ccgtgaagct ggattcgcta gtaatcgcgc atcagccatg   1260
gcgcggtgaa tacgttcccg ggccttgtac acaccgcccg tcaagcca               1308
```

METHOD FOR IDENTIFYING BACTERIA FOR BACTERIOTHERAPY

This application is a U.S. national stage application of International Application No. PCT/GB2013/051298, which was filed on May 20, 2013 with the title "METHODS AND GROUPS", which claims priority to GB 1211961.6 filed Jul. 5, 2012 and GB 1208845.6 filed May 18, 2012, each of which is incorporated by reference in their entireties for all purposes.

INCORPORATION-BY-REFERENCE OF SEQUENCE LISTING

The contents of the text file named "MEWB_022_02US_SubSeqList.txt", which was created on Apr. 16, 2015 and is 14 KB in size, are hereby incorporated by reference in their entireties.

TECHNICAL FIELD

The invention relates to methods and groups of bacterial isolates relevant to bacteriotherapy. In particular, the invention relates to methods for identifying bacterial isolates suitable for bacteriotherapy, to bacterial isolates identified by such methods and to the use of such bacterial isolates in bacteriotherapy.

BACKGROUND

*Clostridium difficile*, an anaerobic, Gram-positive bacterium, is a major cause of antibiotic-associated diarrhea and challenges healthcare infection control measures by producing highly infectious and resistant spores. Antibiotic treatment, advanced age and hospitalization are the major risk factors for *C. difficile* colonization, leading to a spectrum of outcomes ranging from asymptomatic carriage, severe diarrhea, pseudomembranous colitis or even death. Current first line treatments for *C. difficile* disease are vancomycin or metronidazole, although in 20-35% of these cases recurrent disease (relapse or re-infection) follows the cessation of antibiotic therapy. Recurrent *C. difficile* disease is associated with a pathological imbalance within the resident intestinal microbial community, or "dysbiosis", so therapies that restore a healthy microbiota are viewed as promising alternatives. Recurrent *Clostridium difficile* disease in humans is associated with a pathological imbalance within the resident intestinal microbiota, referred to as dysbiosis.

Fecal bacteriotherapy, the administration of homogenized feces from a healthy donor, has been investigated as an alternative therapy for recurrent *C. difficile* disease in humans. However, the mechanism of bacteriotherapy using fecal flora and specific probiotic mix in the feces which are of use in bacteriotherapy has so far been unclear.

SUMMARY

In a first aspect, the invention provides a method, for the identification of bacterial isolates suitable for use in bacteriotherapy, the method comprising:
(i) preparing a suspension of material collected from a host harbouring microbiota;
(ii) addition of an activator of bacterial spores sufficient to allow growth of bacteria from spores present in the suspension;
(iii) culturing the suspension; and
(iv) identification of at least one bacterial isolate within the culture In a second aspect, the invention provides method for preparing fecal material suitable for bacteriotherapy or a method for identification of bacterial isolates suitable for use in bacteriotherapy the method comprising preparing a suspension of fecal material followed by incubation of the suspension in a standing culture under anaerobic or aerobic conditions.

In one aspect, the invention provides a method for preparing material suitable for use in bacteriotherapy, the method comprising:
(i) preparing a suspension of fecal material;
(ii) addition of an activator of bacterial spores sufficient to allow growth of bacteria from spores present in the suspension; and
(iii) culturing the suspension.

In one aspect, the invention provides a group of bacterial isolates suitable for bacteriotherapy obtainable or identifiable according to any of the methods described above and in the rest of this application.

In another aspect, the invention provides a group of bacterial isolates obtainable or identifiable according to the method of any previous aspect of the invention for use in bacteriotherapy.

In another aspect, the invention provides the use of a group of bacterial isolates obtainable or identifiable according to the method of any previous aspect of the invention in the manufacture of a medicament for providing bacteriotherapy.

In another aspect, the invention provides cultured fecal material for use in bacteriotherapy, and/or for identification of bacterial strains suitable for use in bacteriotherapy, wherein the bacteriotherapy is to facilitate repopulation of the gut and/or prevention or treatment of diseases associated with infections or the microbiota, or diseases related thereto, and/or prevention of transmission of infection. In one embodiment the infection is a bacterial infection. In one embodiment the infection is a viral infection. In one embodiment the infection is *C. difficile* infection.

In another aspect, the invention provides a subset of bacteria obtainable or identifiable from fecal material for use in facilitating repopulation of the gut and/or in prevention or treatment of bacterial or viral infections, dysfunction associated with the microbiota or diseases related thereto and/or in prevention of transmission of bacterial or viral infection, wherein the subset comprises 3 to 9, optionally no more than 6, isolates of bacteria.

In another aspect, the invention provides use of 3 to 9, optionally no more 6, bacterial isolates in the preparation of a medicament to facilitate repopulation of the gut and/or in prevention or treatment of bacterial or viral infections, dysfunction associated with the microbiota or diseases related thereto and/or in prevention of transmission of bacterial or viral infection.

In another aspect, the invention provides a composition comprising or consisting essentially of a group of bacterial isolates according to any of the previous aspects. The composition is suitable for providing bacteriotherapy.

In another aspect, the invention provides a method of providing bacteriotherapy, the method comprising delivering to a human or non-human animal a group of bacterial isolates according to any of the previous aspects.

The preferred features may be combined as appropriate, as would be apparent to a skilled person, and may be combined with any of the aspects of the invention.

BRIEF DESCRIPTION OF THE DRAWINGS

Embodiments of the invention will be described, by way of example, with reference to the following drawings, in which:

FIGS. 1A-C. Epidemic *C. difficile* 027/BI induces a persisting supershedder state with enhanced transmissibility compared to other virulent variants FIGS. 2A-B. Fecal bacteriotherapy resolves relapsing *C. difficile* 027/BI-7 disease and host contagiousness FIGS. 3A-C. Effective bacteriotherapy re-establishes a healthy, diverse microbiota profile in epidemic *C. difficile* 027/BI supershedder mice.

FIGS. 13A-C. Rarefaction curves demonstrating observed bacterial diversity of feces from healthy, naïve mice and its serially passaged derivatives.

DETAILED DESCRIPTION

Figure 1C:
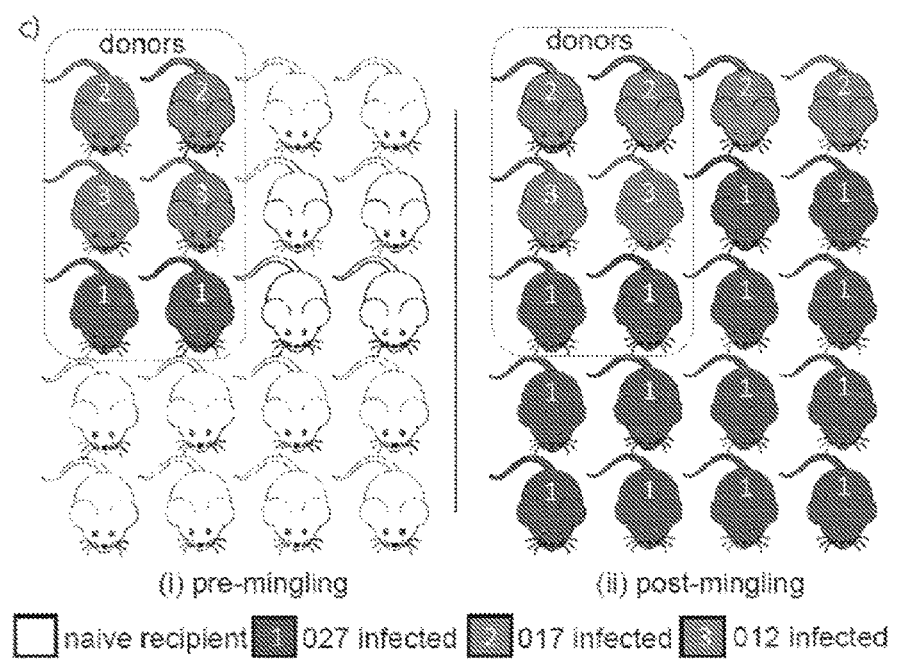

The invention provides methods for identification of desirable bacterial isolates suitable for bacteriotherapy. The invention also provides methods for preparing fecal material suitable for bacteriotherapy.

In one aspect the method may comprise the steps of preparing a suspension of material collected from a host harbouring microbiota, adding an activator of bacterial spores sufficient to allow growth of bacteria from spores present in the suspension and culturing the suspension. The suspension may be cultured under aerobic or anaerobic conditions. The cultured suspension may be incubated in a standing culture under aerobic or anaerobic conditions. In one embodiment, the standing culture is under aerobic conditions.

In one aspect, the method may comprise the steps of preparing a suspension of material followed by incubation of the suspension in a standing culture under aerobic or anaerobic conditions. In one embodiment, the standing culture is under aerobic conditions. An activator of bacterial spores sufficient to allow growth of bacteria from spores may be added to the suspension before the suspension is incubated in a standing culture under aerobic conditions.

The invention also provides methods for identification of bacterial strains suitable for use in bacteriotherapy comprising the steps of any of the previous aspects and comprising the additional step of identification of at least one, preferably a group of, bacterial isolates within the culture.

In one aspect, the invention provides a method for preparing material comprising desirable bacterial isolates, the method comprising preparing a suspension of material collected from a host harbouring microbiota, such as fecal material, by diluting the material in sterile PBS; plating on nutrient agar plates; adding anaerobic culture media and an activator of bacterial spores sufficient to allow growth of bacteria from spores present in the suspension and growing either aerobically or anaerobically at a suitable temperature, such as about 37° C., for 24-72 hours. Distinct colony types may be isolated and culture purified.

In one embodiment, the material being cultured is serially passaged and the material prepared after $1^{st}$ or $2^{nd}$ passage is selected for use in the methods according to the invention. The material collected from a host harbouring microbiota, such as healthy feces, may be passaged overnight in nutrient broth at a suitable temperature, such as about 37° C., to reduce the bacterial community complexity and to enrich for readily culturable bacteria.

In one embodiment, the methods of preparation of identification according to the invention includes incubation of the suspension in a standing culture under aerobic conditions to provide the microbes with an oxygen gradient.

In one embodiment, the culture media used during culturing of the suspension in the methods of preparation of identification according to the invention may be anaerobic culture media.

In one embodiment bacterial isolates according to any previous aspect can be identified from such prepared material by isolating genomic DNA from the distinct colonies and species-level profiling of the intestinal microbiota. The species level profiling may be sequencing specific genes, such as the 16S rRNA gene, and comparing to the GenBank and RDP databases to identify the bacterial species. Whole genome sequencing and phylogenetic analysis of intestinal bacteria can also be carried out to identify common genes between the isolates of interest. The species diversity in each sample may be measured by calculating the Shannon Diversity Index (such as described in P. D. Schloss et al. referenced in the examples section).

In one aspect the bacterial isolate comprises a DNA sequence that encodes 16S rRNA which is one of the following 6 sequences, or which has homology or identity to one of the following 6 sequences, suitably at a level of greater than 85%, such as greater than 86%, greater than 87%, greater than 88%, greater than 89%, greater than 90%, greater than 91%, greater than 92%, greater than 93%, greater than 94%, greater than 95%, greater than 96%, greater than 97%, greater than 98%, greater than 99% or more, across the sequence.

In addition the present invention relates to a bacterial isolate per se comprising a DNA sequence that encodes 16S rRNA having the sequence of SEQ ID Nos. 13, 14 or 18 below.

1318 bp (97% to *Adlercreutzia equolifaciens*)

SEQ ID NO.: 13

ACGGGTGAGTAACACGTGACCAACCTGCCCCGCGCTCCGGGACACCGCTGGAAACGGCGG
CTAATACCGGATACTCCGGGAGGGCCCCATGGCCCTGCCGGGAAAGCCGAGACGGCGCGG
GATGGGGTCGCGGCCCATTAGGTAGACGGCGGGGTAACGGCCCACCGTGCCCGCGATGGG
TAGCCGGACTGAGAGGTCGACCGGCCACATTGGGACTGAGATACGGCCCAGACTCCTACG
GGAGGCAGCAGTGGGGAATTTTGCGCAATGGGGGAACCCTGACGCAGCAACGCCGCGTG
CGGGACGAAGGCCCTCGGGTTGTAAACCGCTTTCAGCAGGGAAGATCCAAGACGGTACCT
GCAGAAGAAGCTCCGGCTAACTACGTGCCAGCAGCCGCGGTAATACGTAGGGGGCGAGCG
TTATCCGGATTCATTGGGCGTAAAGCGCGCGTAGGCGGCCGCCTAAGCGGGACCTCTAAC
CCCGGGGCTCAACCCCGGGCCGGGTCCCGGACTGGGCGGCTCGAGTGCGGTAGAGGAGAG
CGGAATTCCCGGTGTAGCGGTGGAATGCGCAGATATCGGGAAGAACACCGATGGCGAAGG
CAGCTCTCTGGGCCGTCACTGACGCTGAGGCGCGAAAGCTGGGGGAGCGAACAGGATTAG
ATACCCTGGTAGTCCCAGCCGTAAACGATGGGCGCTAGGTGTGGGGGGACGATCCCTCCG
TGCCGCAGCCAACGCATTAAGCGCCCCGCCTGGGGAGTACGGCCGCAAGGCTAAAACTCA
AAGGAATTGACGGGGGCCCGCACAAGCAGCGGAGCATGTGGCTTAATTCGAAGCAACGCG
AAGAACCTTACCAGGGCTTGACATGCCGATGAAGCCGGGGAGACCCGGTGGCCGAGAGGA
GTCGGCGCAGGTGGTGCATGGCTGTCGTCAGCTCGTGTCGTGAGATGTTGGGTTAAGTCC
CGCAACGAGCGCAACCCCCGCCCCGTGTTGCCAGCATTCAGTTGGGGACTCGCGGGGGAC
TGCCGGCGTCAAGCCGGAGGAAGGTGGGGACGACGTCAAGTCATCATGCCCCTTATGCCC
TGGGCTGCACACGTGCTACAATGGCCGGTACAGAGGGTTGCCACCCCGCGAGGGGGAGCG
GATCCCGGAAAGCCGGTCCCAGTTCGGATCGCAGGCTGCAACCCGCCTGCGTGAAGCCGG
AGTTGCTAGTAATCGCGGATCAGCACGCCGCGGTGAATACGTTCCCGGGCCTTGTACACA
CCGCCCGTCACACCACCCGAGTCGTCTGCACCCGAAGCCGCCGGCCGAACCCCCGGGG 1292 bp (98% to *Anaerostipes caccae*)

SEQ ID NO.: 14

AGTGGCGGACGGGTGAGTAACGCGTGGGGAACCTGCCCTATACAGGGGGATAACAGCTGG
AAACGGCTGCTAATACCGCATAAGCGCACAGAATCGCATGATTCGGTGTGAAAAGCTCCG
GCAGTATAGGATGGTCCCGCGTCTGATTAGCTGGTTGGCGGGGTAACGGCCCACCAAGGC
GACGATCAGTAGCCGGCTTGAGAGAGTGGACGGCCACATTGGGACTGAGACACGGCCCAA
ACTCCTACGGGAGGCAGCAGTGGGGAATATTGCACAATGGGGGAAACCCTGATGCAGCGA
CGCCGCGTGAGTGAAGAAGTATTTCGGTATGTAAAGCTCTATCAGCAGGGAAGAAAAAAG
ACGGTACCTGACTAAGAAGCCCCGGCTAACTACGTGCCAGCAGCCGCGGTAATACGTAGG
GGGCAAGCGTTATCCGGAATTACTGGGTGTAAAGGGTGCGTAGGTGGCATGGTAAGTCAG
AAGTGAAAGCCCGGGGCTTAACCCCGGGACTGCTTTTGAAACTGTCATGCTGGAGTGCAG
GAGAGGTAAGCGGAATTCCTAGTGTAGCGGTGAAATGCGTAGATATTAGGAGGAACACCA
GTGGCGAAGGCGGCTTACTGGACTGTCACTGACACTGATGCACGAAAGCGTGGGGAGCAA
ACAGGATTAGATACCCTGGTAGTCCACGCCGTAAACGATGAATACTAGGTGTCGGGCCG
TAGAGGCTTCGGTGCCGCAGCAAACGCAGTAAGTATTCCACCTGGGGAGTACGTTCGCAA
GAATGAAACTCAAAGGAATTGACGGGGACCCGCACAAGCGGTGGAGCATGTGGTTTAATT
CGAAGCAACGCGAAGAACCTTACCTGGTCTTGACATCTAACTGACCGGTTCGTAATGGGA
CCTTTCCTTCGGGACAGTTAAGACAGGTGGTGCATGGTTGTCGTCAGCTCGTGTCGTGAG
ATGTTGGGTTAAGTCCCGCAACGAGCGCAACCCCTATCTTTAGTAGCCAGCATATAAGGT

-continued

GGGCACTCTAGAGAGACTGCCAGGGATAACCTGGAGGAAGGTGGGGACGACGTCAAATCA

TCATGCCCCTTATGGCCAGGGCTACACACGTGCTACAATGGCGTAAACAAAGGGAAGCGA

AGTCGTGAGGCGAAGCAAATCCCAGAAATAACGTCTCAGTTCGGATTGTAGTCTGCAACT

CGACTACATGAAGCTGGAATCGCTAGTAATCGTGAATCAGAATGTCACGGTGAATACGTT

CCCGGGTCTTGTACACACCGCCCGTCACACCA

[1324 bp, 100% to *Staphylococcus warneri*]

SEQ ID NO.: 15

AGCGGCGGACGGGTGAGTAACACGTGGATAACCTACCTATAAGACTGGGATAACTTCGGG

AAACCGGAGCTAATACCGGATAACATATTGAACCGCATGGTTCAATAGTGAAAGGCGGCT

TTGCTGTCACTTATAGATGGATCCGCGCCGTATTAGCTAGTTGGTAAGGTAACGGCTTAC

CAAGGCAACGATACGTAGCCGACCTGAGAGGGTGATCGGCCACACTGGAACTGAGACACG

GTCCAGACTCCTACGGGAGGCAGCAGTAGGGAATCTTCCGCAATGGGCGAAAGCCTGACG

GAGCAACGCCGCGTGAGTGATGAAGGTCTTCGGATCGTAAAACTCTGTTATCAGGGAAGA

ACAAATGTGTAAGTAACTGTGCACATCTTGACGGTACCTGATCAGAAAGCCACGGCTAAC

TACGTGCCAGCAGCCGCGGTAATACGTAGGTGGCAAGCGTTATCCGGAATTATTGGGCGT

AAAGCGCGCGTAGGCGGTTTTTTAAGTCTGATGTGAAAGCCCACGGCTCAACCGTGGAGG

GTCATTGGAAACTGGAAAACTTGAGTGCAGAAGAGGAAAGTGGAATTCCATGTGTAGCGG

TGAAATGCGCAGAGATATGGAGGAACACCAGTGGCGAAGGCGACTTTCTGGTCTGTAACT

GACGCTGATGTGCGAAAGCGTGGGGATCAAACAGGATTAGATACCCTGGTAGTCCACGCC

GTAAACGATGAGTGCTAAGTGTTAGGGGGTTTCCGCCCCTTAGTGCTGCAGCTAACGCAT

TAAGCACTCCGCCTGGGGAGTACGACCGCAAGGTTGAAACTCAAAGGAATTGACGGGGAC

CCGCACAAGCGGTGGAGCATGTGGTTTAATTCGAAGCAACGCGAAGAACCTTACCAAATC

TTGACATCCTTTGACCGCTCTAGAGATAGAGTCTTCCCCTTCGGGGGACAAAGTGACAGG

TGGTGCATGGTTGTCGTCAGCTCGTGTCGTGAGATGTTGGGTTAAGTCCCGCAACGAGCG

CAACCCTTAAGCTTAGTTGCCATCATTAAGTTGGGCACTCTAAGTTGACTGCCGGTGACA

AACCGGAGGAAGGTGGGGATGACGTCAAATCATCATGCCCCTTATGATTTGGGCTACACA

CGTGCTACAATGGACAATACAAAGGGCAGCTAAACCGCGAGGTCAAGCAAATCCCATAAA

GTTGTTCTCAGTTCGGATTGTAGTCTGCAACTCGACTACATGAAGCTGGAATCGCTAGTA

ATCGTAGATCAGCATGCTACGGTGAATACGTTCCCGGGTCTTGTACACACCGCCCGTCACACCA 1323 bp, 100% to *Lactobacillus reuteri*

SEQ ID NO.: 16

AGTGGCGGACGGGTGAGTAACACGTAGGTAACCTGCCCCGGAGCGGGGGATAACATTTGG

AAACAGATGCTAATACCGCATAACAACAAAAGCCACATGGCTTTTGTTTGAAAGATGGCT

TTGGCTATCACTCTGGGATGGACCTGCGGTGCATTAGCTAGTTGGTAAGGTAACGGCTTA

CCAAGGCGATGATGCATAGCCGAGTTGAGAGACTGATCGGCCACAATGGAACTGAGACAC

GGTCCATACTCCTACGGGAGGCAGCAGTAGGGAATCTTCCACAATGGGCGCAAGCCTGAT

GGAGCAACACCGCGTGAGTGAAGAAGGGTTTCGGCTCGTAAAGCTCTGTTGTTGGAGAAG

AACGTGCGTGAGAGTAACTGTTCACGCAGTGACGGTATCCAACCAGAAAGTCACGGCTAA

CTACGTGCCAGCAGCCGCGGTAATACGTAGGTGGCAAGCGTTATCCGGATTTATTGGGCG

TAAAGCGAGCGCAGGCGGTTGCTTAGGTCTGATGTGAAAGCCTTCGGCTTAACCGAAGAA

GTGCATCGGAAACCGGGCGACTTGAGTGCAGAAGAGGACAGTGGAACTCCATGTGTAGCG

GTGGAATGCGTAGATATATGGAAGAACACCAGTGGCGAAGGCGGCTGTCTGGTCTGCAAC

```
TGACGCTGAGGCTCGAAAGCATGGGTAGCGAACAGGATTAGATACCCTGGTAGTCCATGC

CGTAAACGATGAGTGCTAGGTGTTGGAGGGTTTCCGCCCTTCAGTGCCGGAGCTAACGCA

TTAAGCACTCCGCCTGGGGAGTACGACCGCAAGGTTGAAACTCAAAGGAATTGACGGGGG

CCCGCACAAGCGGTGGAGCATGTGGTTTAATTCGAAGCTACGCGAAGAACCTTACCAGGT

CTTGACATCTTGCGCTAACCTTAGAGATAAGGCGTTCCCTTCGGGGACGCAATGACAGGT

GGTGCATGGTCGTCGTCAGCTCGTGTCGTGAGATGTTGGGTTAAGTCCCGCAACGAGCGC

AACCCTTGTTACTAGTTGCCAGCATTAAGTTGGGCACTCTAGTGAGACTGCCGGTGACAA

ACCGGAGGAAGGTGGGGACGACGTCAGATCATCATGCCCCTTATGACCTGGGCTACACAC

GTGCTACAATGGACGGTACAACGAGTCGCAAGCTCGCGAGAGTAAGCTAATCTCTTAAAG

CCGTTCTCAGTTCGGACTGTAGGCTGCAACTCGCCTACACGAAGTCGGAATCGCTAGTAA

TCGCGGATCAGCATGCCGCGGTGAATACGTTCCCGGGCCTTGTACACACCGCCCGTCACACCA 1323 bp, 100% Enterococcus hirae
                                                SEQ ID NO.: 17
AGTGGCGAACGGGTGAGTAACACGTGGGTAACCTGCCCATCAGAAGGGGATAACACTTGG

AAACAGGTGCTAATACCGTATAACAATCGAAACCGCATGGTTTCGATTTGAAAGGCGCTT

TCGGGTGTCGCTGATGGATGGACCCGCGGTGCATTAGCTAGTTGGTGAGGTAACGGCTCA

CCAAGGCGACGATGCATAGCCGACCTGAGAGGGTGATCGGCCACATTGGGACTGAGACAC

GGCCCAAACTCCTACGGGAGGCAGCAGTAGGGAATCTTCGGCAATGGACGAAAGTCTGAC

CGAGCAACGCCGCGTGAGTGAAGAAGGTTTTCGGATCGTAAAACTCTGTTGTTAGAGAAG

AACAAGGATGAGAGTAACTGTTCATCCCTTGACGGTATCTAACCAGAAAGCCACGGCTAA

CTACGTGCCAGCAGCCGCGGTAATACGTAGGTGGCAAGCGTTGTCCGGATTTATTGGGCG

TAAAGCGAGCGCAGGCGGTTTCTTAAGTCTGATGTGAAAGCCCCCGGCTCAACCGGGGAG

GGTCATTGGAAACTGGGAGACTTGAGTGCAGAAGAGGAGAGTGGAATTCCATGTGTAGCG

GTGAAATGCGTAGATATATGGAGGAACACCAGTGGCGAAGGCGGCTCTCTGGTCTGTAAC

TGACGCTGAGGCTCGAAAGCGTGGGGAGCAAACAGGATTAGATACCCTGGTAGTCCACGC

CGTAAACGATGAGTGCTAAGTGTTGGAGGGTTTCCGCCCTTCAGTGCTGCAGCTAACGCA

TTAAGCACTCCGCCTGGGGAGTACGACCGCAAGGTTGAAACTCAAAGGAATTGACGGGGG

CCCGCACAAGCGGTGGAGCATGTGGTTTAATTCGAAGCAACGCGAAGAACCTTACCAGGT

CTTGACATCCTTTGACCACTCTAGAGATAGAGCTTCCCCTTCGGGGGCAAAGTGACAGGT

GGTGCATGGTTGTCGTCAGCTCGTGTCGTGAGATGTTGGGTTAAGTCCCGCAACGAGCGC

AACCCTTATTGTTAGTTGCCATCATTCAGTTGGGCACTCTAGCAAGACTGCCGGTGACAA

ACCGGAGGAAGGTGGGGATGACGTCAAATCATCATGCCCCTTATGACCTGGGCTACACAC

GTGCTACAATGGGAAGTACAACGAGTCGCAAAGTCGCGAGGCTAAGCTAATCTCTTAAAG

CTTCTCTCAGTTCGGATTGTAGGCTGCAACTCGCCTACATGAAGCCGGAATCGCTAGTAA

TCGCGGATCAGCACGCCGCGGTGAATACGTTCCCGGGCCTTGTACACACCGCCCGTCACACCA 1308 bp (87% to Barnesiella intestinihominis)
                                                SEQ ID NO.: 18
ACCGGCGCACGGGTGAGTAACACGTATGCAACCTGCCCTCTTCAGGGGGACAACCTTCCG

AAAGGGAGGCTAATCCCGCGTATATCGGTTTCGGGCATCCGTTATCGAGGAAAGATTCAT

CGGAAGAGGATGGGCATGCGGCGCATTAGCTTGACGGCGGGGTAACGGCCCACCGTGGCG

ACGATGCGTAGGGGTTCTGAGAGGAAGGTCCCCCACACTGGTACTGAGACACGGACCAGA

CTCCTACGGGAGGCAGCAGTGAGGAATATTGGTCAATGGGAGAGATCCTGAACCAGCCAA

GCCGCGTGAGGGAAGACGGCCCTATGGGTTGTAAACCTCTTTTGTCGGAGAACAAAACCC
```

-continued

```
GGGACGAGTCCCGGACTGCGTGTATCCGAAGAAAAAGCATCGGCTAACTCCGTGCCAGCA

GCCGCGGTAATACGGAGGATGCGAGCGTTATCCGGATTTATTGGGTTTAAAGGGTGCGTA

GGCGGTCCGTTAAGTCAGCGGTAAAATTGCGGGGCTCAACCCCGTCGAGCCGTTGAAACT

GGCAGACTTGAGTTGGCGAGAAGTACGCGGAATGCGCGGTGTAGCGGTGAAATGCATAGA

TATCGCGCAGAACTCCGATTGCGAAGGCAGCGTACCGGCGCCAGACTGACGCTGAGGCAC

GAAAGCGTGGGGATCGAACAGGATTAGATACCCTGGTAGTCCACGCAGTAAACGATGAAT

GCTAGGTGTCCGGGTCGAATGAGACCTGGGCGGCGAAGCGAAAGCGATAAGCATTCCACC

TGGGGAGTACGCCGGCAACGGTGAAACTCAAAGGAATTGACGGGGGCCCGCACAAGCGGA

GGAACATGTGGTTTAATTCGATGATACGCGAGGAACCTTACCCGGGCTCAAACGGGAGTG

GAATGGACCAGAGACGGTTCAGCCTACGGGCCGCTTCCGAGGTGCTGCATGGTTGTCGTC

AGCTCGTGCCGTGAGGTGTCGGCTTAAGTGCCATAACGAGCGCAACCCCCGCCGGCAGTT

GCTAACGGGCAATGCCGAGGACTCTGCCGGGACTGCCGCCGCAAGGCGTGAGGAAGGCGG

GGATGACGTCAAATCAGCACGGCCCTTACGTCCGGGGCGACACACGTGTTACAATGGGCG

GTACAGCGGGAAGCCAGGCGGCGACGCCGAGCGGAACCCGAAAGCCGTTCTCAGTTCGGA

TCGGAGTCTGCAACCCGACTCCGTGAAGCTGGATTCGCTAGTAATCGCGCATCAGCCATG

GCGCGGTGAATACGTTCCCGGGCCTTGTACACACCGCCCGTCAAGCCA
```

In one embodiment, the individual isolates identified in the resulting cultured suspension are assessed in combinations to identify subsets of the cultured suspension for use in, or suitable for use in, bacteriotherapy. Suitability of a bacterial isolate for bacteriotherapy may be assessed by administration of the isolates or groups of isolates to the recipient and measuring a shift in the recipients' microbiota to a composition similar to that of a healthy microbiota. The shift in recipients' microbiota is linked to increase in species diversity which can be measured by calculating the Shannon Diversity Index described in the example below.

In one embodiment, bacterial isolates suitable for bacteriotherapy according to any previous aspect can be identified by in vivo assessment, for example in an animal model, such as a mouse model, or in a human challenge model with an intestinal phase. In one embodiment, bacterial isolates suitable for bacteriotherapy according to any previous aspect can be identified by assessment of the UTI tract. Such identified isolates can be sequenced as described herein to determine speciation and phylogenetic position.

In one embodiment, the bacterial isolates are initially identified according to a method described above while the actual isolates used for bacteriotherapy are previously characterized isolates of the identified isolates. The previously characterized isolates may be obtained from a biobank of previously identified bacteria assessed to be suitable for bacteriotherapy using the procedures described herein. Restoration of a healthy microbiota with bacteriotherapy is viewed as a promising alternative treatment for recurrent C. difficile disease and other forms of intestinal dysbiosis but it is not widely used because of the time required to identify a suitable donor, the risk of introducing opportunistic pathogens as well as a general patient aversion. The inventors have demonstrated that it is also possible to eradicate C. difficile disease and contagiousness using a simple mixture of defined, culturable, components of the microbiota.

The material collected from a host may be fecal material or material obtained by biopsy or sampling from the gut of the host. The material may be from the intended recipient of bacteriotherapy prior to the need for bacteriotherapy or from a healthy donor. The donor may be a spouse or a member of the bacteriotherapy recipient's immediate family. A healthy donor for the purpose of this invention is an individual not suffering from an infection, such as C. difficile infection, resulting in decreased heterogeneity of intestinal flora.

In one embodiment, the prepared suspension is administered to the recipient or used for identification of bacterial strains within 10 minutes to 2 hours after preparation. In one embodiment the prepared suspension is administered or used within about 30 minutes after preparation. In one embodiment, no more than 6 hours should have elapsed between material collection and administration to the recipient or identification of bacterial strains.

In one embodiment, the cultured suspension or subset thereof comprises a spore forming bacteria.

Addition of an activator of bacterial spores sufficient to allow growth of bacteria from spores is an embodiment of the methods according to the invention. The activator may be a cholate derivative or may comprise one or more cholate derivatives such as taurocholate and/or glycocholate. In one embodiment the activator may comprise a cholate derivative, such as taurocholate, and glycine.

An activator of bacterial spores is expected to stimulate metabolically dormant spores to begin growth. Therefore, addition of an activator of bacterial spores to the medium increases the chances of isolating such fastidious bacteria from the sample.

The invention also relates to a group of bacterial isolates suitable for bacteriotherapy obtainable or identifiable by the method of any of the previously described aspects.

The group may comprise 3, 4, 5, 6, 7, 8 or 9 bacterial isolates. In one embodiment, the group comprises 4, 5 or 6 bacterial isolates. In one embodiment, the group comprises 6 bacterial isolates. In one embodiment, the group comprises no more than 6 bacterial strains. In one embodiment, the group comprises at least 4 bacterial strains.

The group of bacterial isolates may comprise one or more of the following: *Barnesiella intestinihominis, Lactobacillus reuteri, Enterococcus hirae/faecium/durans, Anaerostipes caccae/Clostridium indolis, Staphylococcus warneri/pasteuri, Adlercreutzia equolifaciens, Anaerostipes caccae/ Clostridium indolis, Staphylococcus warneri/pasteuri* and *Barnesiella intestinihominis*. In one embodiment, the group of bacterial isolates comprises *Barnesiella intestinihominis, Lactobacillus reuteri, Enterococcus hirae/faecium/durans, Anaerostipes caccae/Clostridium indolis* and *Staphylococcus warneri/pasteuri*. In one embodiment, the group of bacterial isolates comprises *Staphylococcus warneri, Enterococcus hirae, Lactobacillus reuteri, Anaerostipes* sp., Bacteroidetes sp. and *Enterorhabdus* sp. In one embodiment, the group of bacterial isolates comprises or consists 2, 3, 4, 5, 6, 7, 8 or 9, such as 5 or 6, of these isolates. In one embodiment the group of bacterial isolates comprises or consists of 4, 5 or 6 isolates and includes *Enterococcus hirae, Lactobacillus reuteri*, and Bacteroidetes sp. In one embodiment the group of bacterial isolates comprises or consists of 4, 5 or 6 isolates and includes members of the phyla Firmicutes and Bacteroidetes optionally with members of the phyla Actinobacteria and Proteobacteria.

In another aspect, the invention provides a composition comprising or consisting essentially of a group of bacterial isolates according to any of the previous aspects. The composition is suitable for providing bacteriotherapy.

In one aspect, the group of bacterial isolates or composition according to the invention is for use in bacteriotherapy.

In one aspect, the invention provides a subset of bacteria obtainable or identifiable from fecal material for use in bacteriotherapy wherein the subset comprises 3 to 9, such as 4 to 6, such as no more than 6, isolates of bacteria.

In one aspect, the invention relates to a method of providing bacteriotherapy, the method comprising delivering to a human or non-human animal a group of bacterial isolates or a composition according to any aspect of the invention.

In one aspect, the invention provides use of a group of bacterial isolates according to the invention in the manufacture of a medicament for providing bacteriotherapy. In one embodiment no more 6 bacterial strains are used in the preparation of the medicament.

In one aspect, the invention provides aerobically cultured fecal material for use in bacteriotherapy, and/or for identification of bacterial isolates suitable for use in bacteriotherapy.

Bacteriotherapy refers to the use of a mixture of bacteria to resolve a pathological imbalance within the microbiota of an individual. The mixture may be a mixture of live bacteria obtained from an external source (other human, animal, in vitro culture etc.). In the context of this invention bacteriotherapy may also refer to increasing species diversity of the colonic flora by introducing healthy bacterial flora into a recipient. Healthy bacterial flora refers to heterogeneous intestinal flora such as that present in an individual not suffering from a bacterial infection, such as *C. difficile* infection, resulting in decreased heterogeneity of intestinal flora. The bacteriotherapy may be to facilitate repopulation of the gut with healthy bacterial flora and/or to prevent or treat bacterial or viral infections, or diseases related thereto, and/or to prevent the transmission of bacterial or viral infection.

The bacteriotherapy may be for the prevention or treatment of any disorder influenced by micobiota, such as intestinal disorders. In one embodiment the bacteriotherapy may be for the treatment a *C. difficile* bacterial infection or prevention of transmission of *C. difficile*. In one embodiment the bacteriotherapy may be for the treatment *C. Difficile* syndromes such as recurrent diarrhea, colitis, pseudomembranous colitis. The bacteriotherapy may be for the treatment of intestinal diseases such as inflammatory bowel disease or irritable bowel syndrome. Further, bacteriotherapy can be used to treat obesity. Because the gut micriobiota in obese individuals is different from non-obese individuals, and because gut micriobiota influences energy metabolism, displacing the gut micriobiota of an obese individual with the guy micriobiota of a non-obese individual. In one embodiment the bacteriotherapy may be for restoring intestinal flora disrupted by antibiotic treatment.

As such the group of bacterial isolates, medicaments or compositions according to the invention, may be for use in therapeutic or preventative bacteriotherapy (eg to treat a dysbiotic state or promote maintenance of a healthy microbiota), for example for use in the treatment or prevention of recurrent diarrhoea, colitis, pseudomembranous colitis; ulcerative colitis; pouchitis; antibiotic induced diarrhoea; viral infection; obesity; inflammatory bowel disease, Crohn's disease or irritable bowel syndrome, optionally where the treatment is of a *C. Difficile* syndrome which causes or is associated with the disorder.

The bacterial isolates, medicaments or compositions according to the invention may be delivered by means of a gastro-resistant capsule (e.g., acid-bio resistant to reach the intestinal tract, having a sterile outside) an enteric tube, duodenal tube, nasogastric tube or colonoscope. Capsules may be prepared by techniques such as microencapsulation described in U.S. Pat. No. 5,733,568.

Treatments or specific processes can be applied to improve the stability or viability of the bacterial isolates in the composition. The bacterial isolates can be applied in a dry form or in a wet from. The bacterial isolates may be lyophilized.

The compositions may comprise a dose demonstrated to have a physiological effect, such as between $10^4$ and $10^{11}$ colony forming units (CFU) per g of the dry composition. In one embodiment, the composition comprises between $10^6$ and $5 \times 10^{11}$ CFU/g.

The bacterial isolates or medicaments according to the invention may be provided at a dose of 1-50 g/day, such as 5, 10, 15, 20 or 25 g/day.

Bacteriothepary according to the invention may be combined with other treatments. The other treatment can include antibiotic treatment, such as with antimicrobials including metronidazole, vancomycin or rifamycin, and treatment with immunoglobulins. In an example, bacteriotherapy to treat *C. difficile* or one or more other diseases or afflictions of the digestive tract can be provided using a combination of antibiotics and/or antacid and re-population of a healthy or desired bacterial flora.

In one aspect, a kit of parts can be created to aid in the methods of the invention. The donation kit can include equipment for collection of material from the host. Because much of gut micriobiota is anaerobic, many organisms can die with exposure to air. In an example, the kit can include materials to ship the collected material without harming the samples (e.g., quick freeze, dry ice, etc.). The kit may include the processed material or treatment in a sterile container, such as a nasogastric (NG) tube, a vial (e.g., for use with a retention enema), a gastro-resistant capsule (e.g., acid-bio resistant to reach the intestinal tract, having a sterile outside), etc.

Recipients of bacteriotherapy according to the invention may be humans or non-human animals.

It will be understood that particular aspects and embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. The use of the word "a" or an when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In one aspect such open ended terms also comprise within their scope a restricted or closed definition, for example such as "consisting essentially of", or "consisting of". The term "or combinations thereof" as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims. All documents referred to herein are incorporated by reference to the fullest extent permissible. Any element of a disclosure is explicitly contemplated in combination with any other element of a disclosure, unless otherwise apparent from the context of the application.

The present invention is further described by reference to the following examples, not limiting upon the present invention.

Example

Rational Design of a Simple, Defined Bacteriotherapy that Cures *Clostridium difficile* Disease Summary Recurrent *Clostridium difficile* disease in humans is associated with a pathological imbalance within the resident intestinal microbiota, referred to as dysbiosis. We show that infection of mice with epidemic *C. difficile* (genotype 027/BI) resulted in chronic intestinal disease that was associated with persistent dysbiosis and a highly contagious state. Epidemic *C. difficile* 027/BI infection was refractory to vancomycin treatment, resulting in recurrent disease. In contrast, treatment of *C. difficile* 027/BI infected mice with feces from healthy mice rapidly eradicated *C. difficile* by restoring a diverse, healthy microbiota leading to the resolution of disease and contagiousness. We used this model to design a simple mixture of six phylogenetically diverse intestinal bacteria, including novel species, which can re-establish a health-associated microbiota and eradicate *C. difficile* 027/BI from infected mice as effectively as whole fecal transplants. Thus, we demonstrate a rational approach to harness the therapeutic potential of health-associated microbial communities and to refine bacteriotherapy-based treatments for *C. difficile* disease and potentially other forms of intestinal dysbiosis.

During the past decade a distinct genetic variant of *C. difficile*, genotyped as PCR-ribotype 027 or REA group BI, emerged and caused healthcare-associated epidemics within North America, Europe, Australia and beyond (7, 8). Epidemic *C. difficile* 027/BI is associated with high-level toxin production (9) FIG. 5) severe disease and high rates of recurrence (10, 11). Here we show that infection of C57BL/6 mice with a representative epidemic *C. difficile* 027/BI (strain BI-7) isolate (8) resulted in chronic intestinal disease that was characterized by a pathological inflammatory response (FIG. 1a and FIG. 6). *C. difficile* 027/BI infected mice were also characterized by a highly contagious state ($>10^8$ CFU *C. difficile*/gram feces), which we refer to as a "persisting supershedder" state, that lasted for months (FIG. 1b). In comparison, infection of mice with other variants of human virulent *C. difficile*, including PCR-ribotypes 012 (strain 630) and 017 (strain M68) (8), resulted in self-limiting intestinal disease and a transient contagious state (FIG. 1b) (12, 13). Indeed, the co-housing of mice infected with *C. difficile* 027/BI-7, 017/M68 or 012/630 together with naïve mice for 30 days resulted in the majority (86%) of naïve mice becoming infected with epidemic *C. difficile* 027/BI-7 (FIG. 1c). Therefore, the ability of epidemic *C. difficile* 027/BI-7 to induce chronic intestinal disease and a persistent supershedder state provides a competitive advantage over other variants within a susceptible host population.

Vancomycin treatment of *C. difficile* 027/BI persistent supershedders rapidly suppressed *C. difficile* excretion to below the culture detection limit (FIG. 2a), as expected because *C. difficile* 027/BI-7 is susceptible to vancomycin. However, cessation of vancomycin treatment was followed within 5-7 days by a relapse (by the same strain) to high-level C. difficile shedding (>$10^8$ CFU/gram) in all mice (n=120) (FIG. 2a). Relapse occurred even after mice were moved to individual sterile cages to reduce host-to-host transmission and re-colonization by environmental spores. The relapsing supershedder state caused by C. difficile 027/BI was very robust since it occurred in mice of different genetic backgrounds (FIG. 7; Table 1). Thus, we show for the first time that natural infection of mice with epidemic C. difficile 027/BI mimics many aspects of recurrent disease and host-to-host transmission observed in humans.

Figure 8:
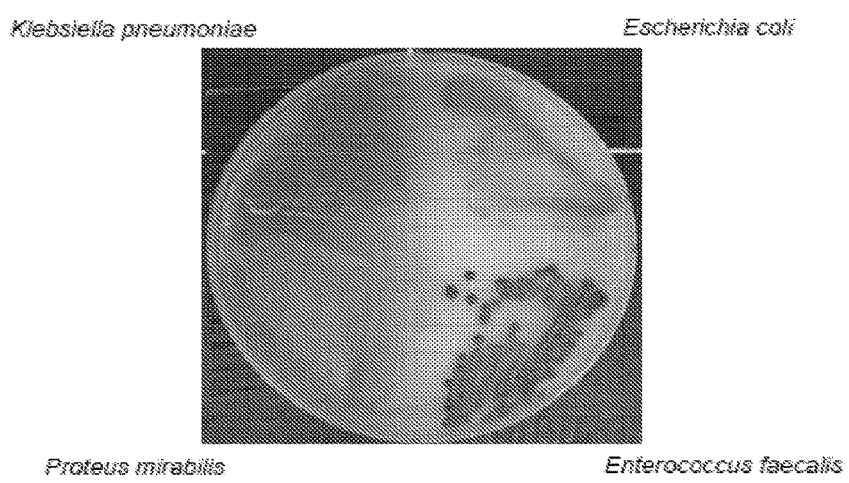

Fecal bacteriotherapy, the administration of homogenized feces from a healthy donor, has been investigated as an alternative therapy for recurrent C. difficile disease in humans (6, 14). Therefore, we tested the ability of fecal bacteriotherapy to suppress the C. difficile 027/BI supershedder state in mice. A single oral treatment of C. difficile 027/BI-7 supershedding mice with homogenized feces from a healthy donor rapidly (4-7 days) and robustly (23 of 25 attempts) suppressed C. difficile shedding levels to below culture detection limits and, in contrast to vancomycin therapy, this lasted for months (FIG. 2a). In comparison, treatment of supershedders with PBS, autoclaved feces, fecal filtrate, short chain fatty acids or laboratory E. coli had a negligible effect on C. difficile shedding levels (FIG. 8). Importantly, suppression of C. difficile shedding levels using feces from healthy mice was consistently associated with a complete loss of contagiousness (FIG. 2b), a resolution of intestinal pathology and a reduced expression of proinflammatory genes (FIG. 2c).

Figures 3, 3A:
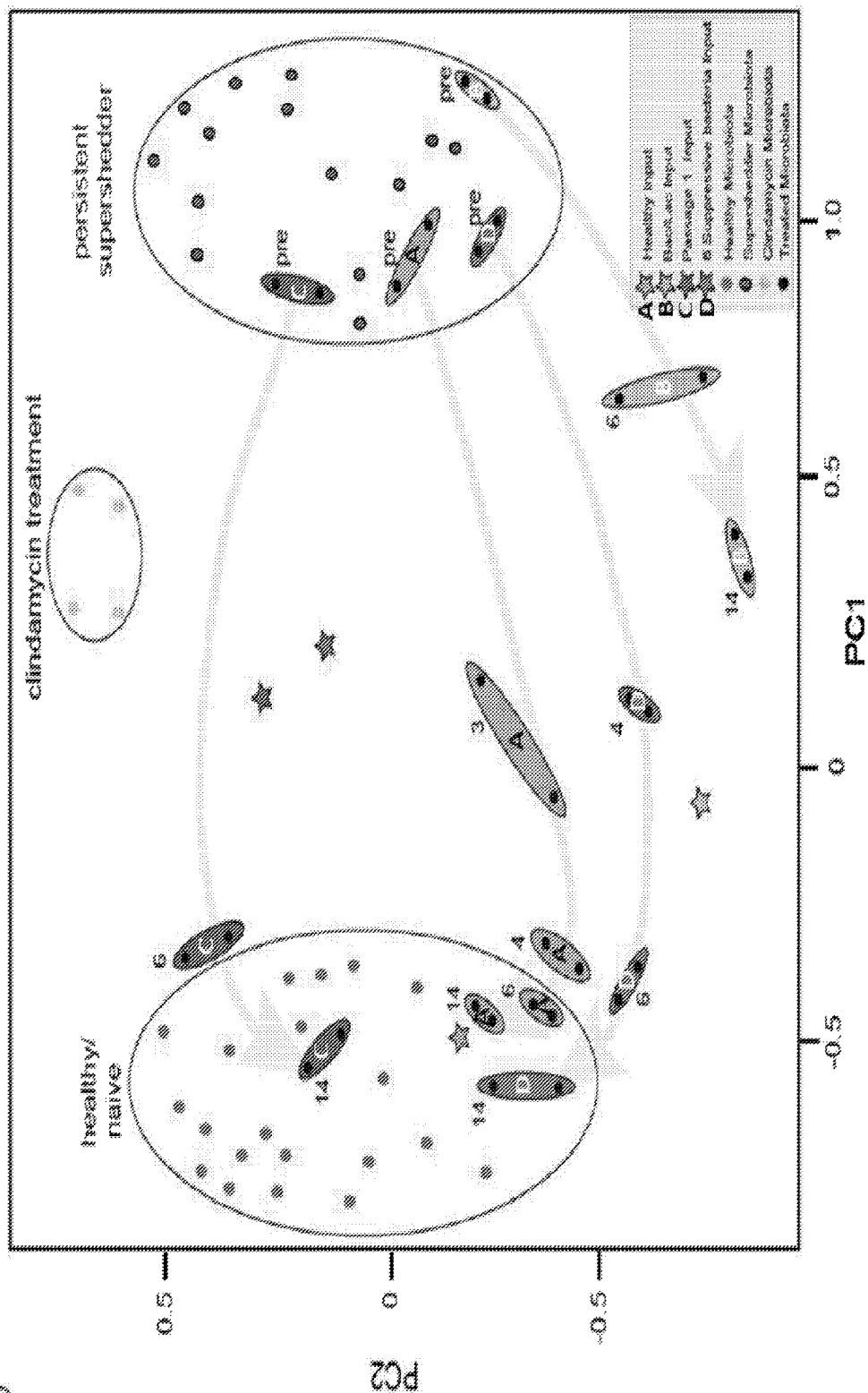
Figure 7:
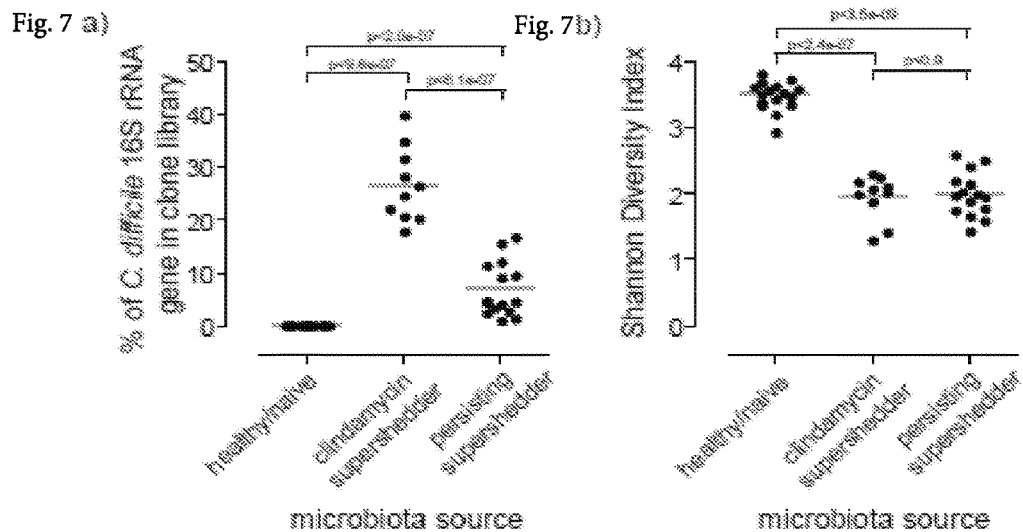
FIGS. 7A-B. Epidemic *C. difficile* 027/BI-7 induces intestinal dysbiosis in mice FIG. 8. Impact of various oral treatments on epidemic *C. difficile* 027/BI supershedder state in mice.
Figure 9:
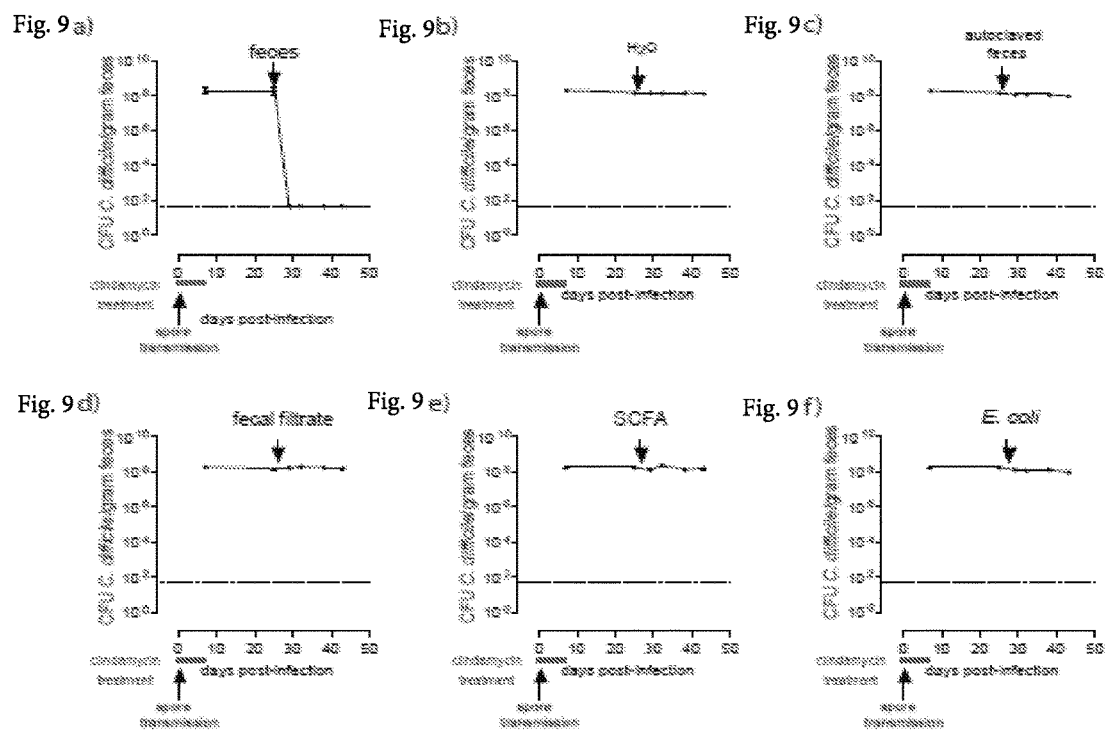
FIGS. 9A-F. Distinct intestinal microbiota community structures from healthy/naïve mice (n=17), clindamycin supershedders (*C. difficile* 027/BI-7 infected mice on clindamycin; n=10) and persisting supershedders (*C. difficile* 027/BI-7 infected mice not on clindamycin; n=17)

We hypothesized that the persistent supershedder state caused by C. difficile 027/BI-7 is linked to intestinal dysbiosis, which is resolved by health-associated bacteria present within fecal transplants. Therefore, we performed species-level profiling of the intestinal microbiota of mice (based on the 16S rRNA gene) and demonstrated that distinct microbiota profiles are indeed associated with either "healthy/naïve" mice, "persistent supershedders" or mice undergoing "clindamycin treatment" (FIG. 3a). The microbiota of healthy mice was characterized by high species diversity (FIG. 7) whereas during clindamycin treatment of naïve mice the microbiota was simplified in composition and had an increased proportional abundance of groups such as Enterobacteriaceae (FIGS. 7 and 9). The microbiota from persistent C. difficile 027/BI-7 supershedders was also simplified in structure (FIGS. 7 and 9), however, it consistently contained 16S rRNA gene sequences derived from C. difficile and Blautia producta and regularly generated 16S rRNA gene sequences representative of well known opportunistic pathogens that have been identified within the microbiota of humans with C. difficile disease (4, 15), including Klebsiella pneumoniae, Escherichia coli, Proteus mirabilis, Parabacteroides distasonis and Enterococcus faecalis (Table 1 and FIGS. 7 and 9 and 10). In addition, the microbiota-derived metabolic profile of persistent supershedder mice was significantly altered compared to healthy mice (FIG. 7b). Significantly, we could reproducibly transplant the supershedder microbiota into germ-free mice and the supershedder microbiota structure was maintained, leading to intestinal pathology and a highly contagious state (data not shown), Therefore, C. difficile 027/BI supershedders harbor a stable, persistent and dysbiotic intestinal microbiota.

Figure 11:
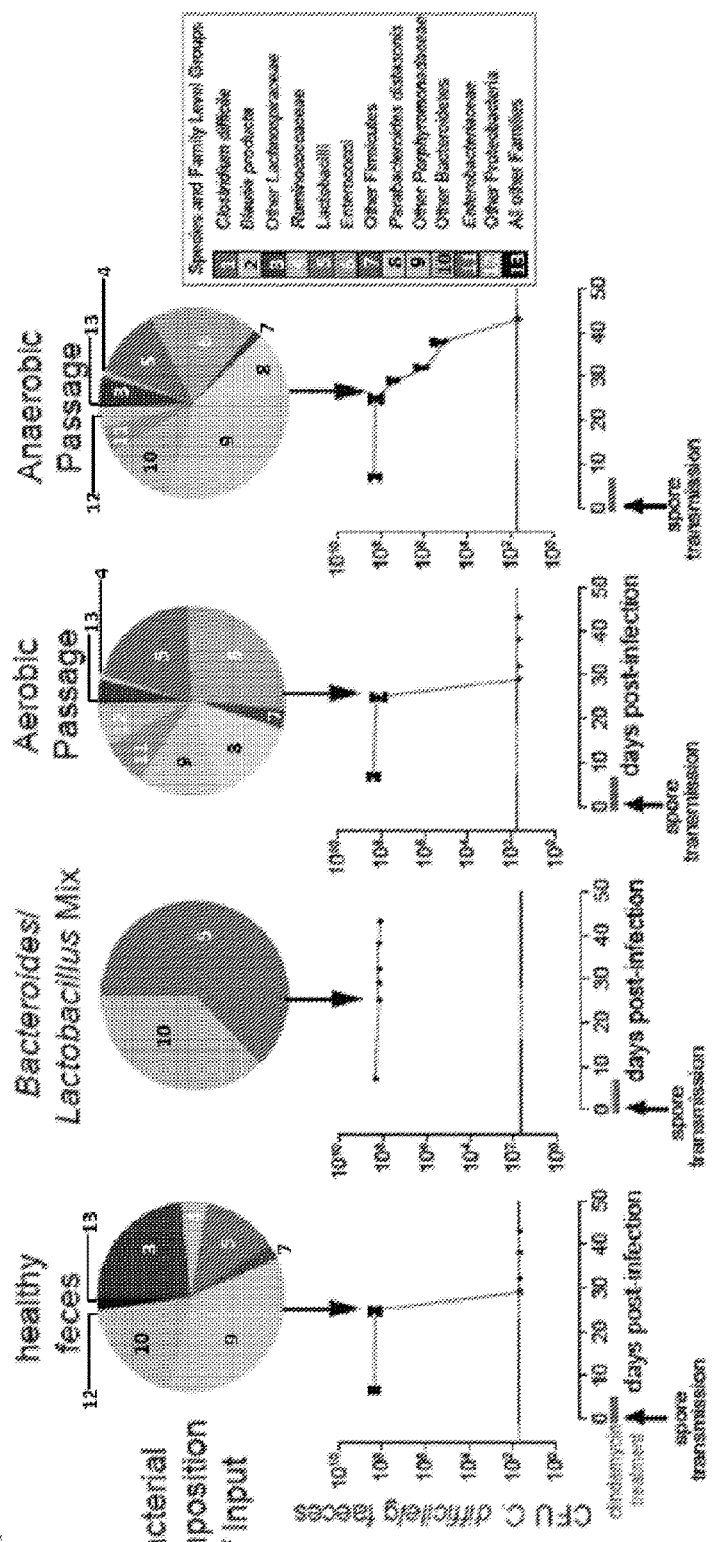
FIGS. 11A-B. Fecal bacteriotherapy suppresses *C. difficile* intestinal colonization and diversifies the intestinal bacterial community of supershedder mice.
Figure 11B:
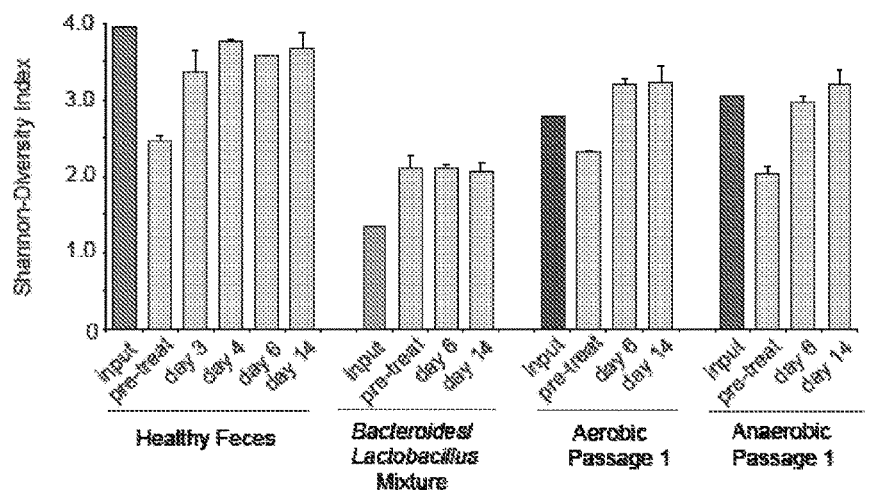
Figure 12:
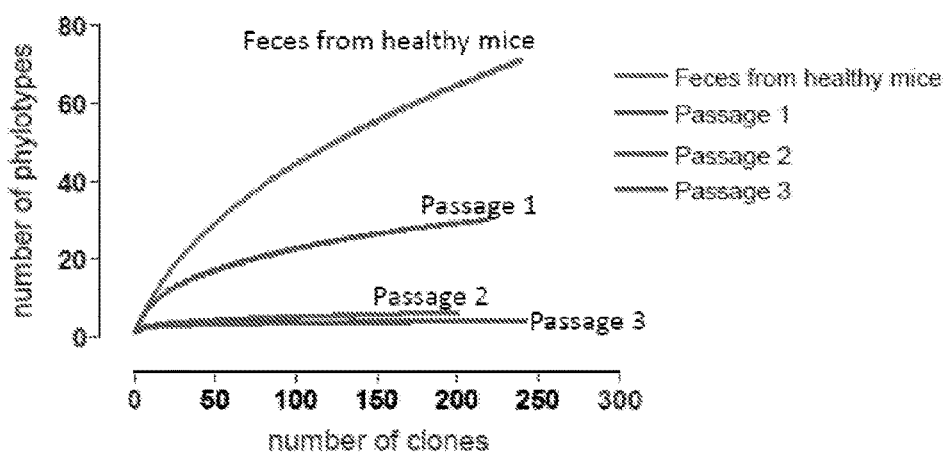
FIG. 12. Simplified fecal derivatives enriched for easily culturable components effectively suppress the epidemic *C. difficile* supershedder 027/BI state in mice.

Next we monitored changes in the supershedders' microbiota after fecal bacteriotherapy. Suppression of C. difficile shedding levels was associated with a shift in the recipients' supershedder microbiota to a composition similar to that of a healthy microbiota (FIG. 3a) and this was closely linked to a rapid increase in species diversity (FIGS. 11 and 12). Consequently, we reasoned that there are key bacteria within the microbiota of healthy mice that are responsible for suppressing the C. difficile 027/BI supershedder state. To identify candidate bacteria we passaged healthy feces overnight in nutrient broth at 37° C. to reduce the community complexity (FIG. 13) and to enrich for readily culturable bacteria. Treatment of supershedder mice with cultured fecal derivatives serially passaged twice (Passage 1 and 2) effectively suppressed the supershedder state (FIG. 12) and shifted their microbiota composition towards a healthy microbiota profile (FIG. 3a). However, a third passage (Passage 3) resulted in a loss of the protective effects of the fecal derivative against the C. difficile 027/BI supershedder state. These results confirm the presence of culturable bacteria within the microbiota of healthy mice that can suppress C. difficile 027/BI infection as effectively as whole fecal bacteriotherapy.

Figure 3B:
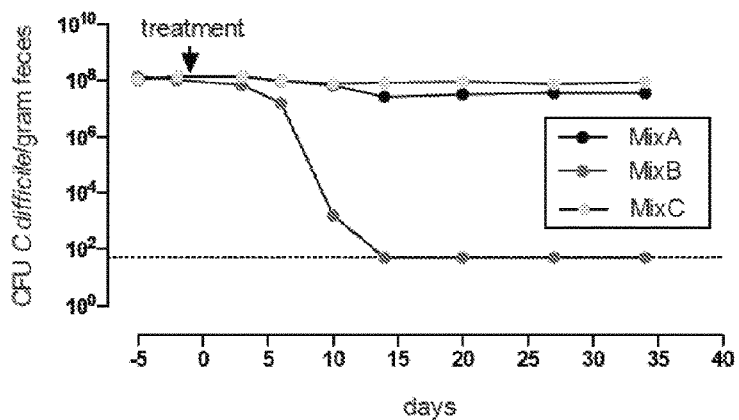
Figure 3C:
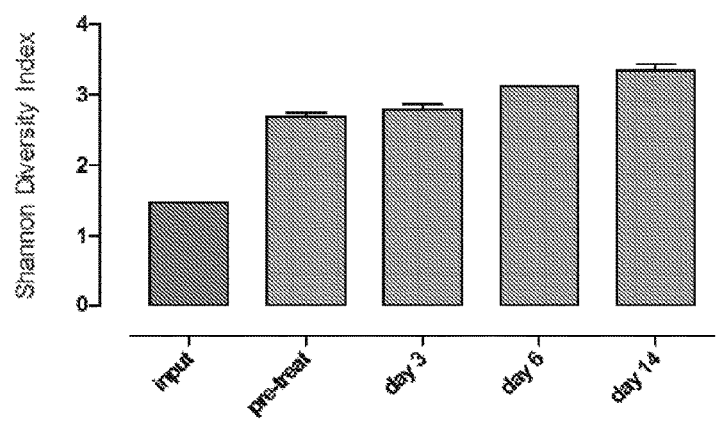

Next, we cultured a diverse collection of 18 bacterial species from the Passage 1 fecal derivative, including representatives of the four phyla that constitute the majority of the mammalian intestinal microbiota (Firmicutes, Bacteroidetes, Actinobacteria and Proteobacteria; Table 2). Then we performed a series of reductive analysis experiments in persistent supershedder mice testing different combinations of bacteria while maximizing the phylogenetic diversity in each mixture (mixtures summarized in table 2). Ultimately we identified a simple, defined mixture of six bacteria that effectively and reproducibly (20/20 mice) suppressed the C. difficile 027/BI supershedder state ("MixB"; FIG. 3b). Significantly, treatment of supershedders with the MixB bacteria shifted the recipients' intestinal microbiota to the profile of a healthy profile (FIG. 3a) and triggered an increase in bacterial diversity that was associated with resolution of intestinal disease and contagiousness (FIG. 3c). Analysis of 16S rRNA gene sequences derived from treated mice confirmed the presence of four of the six MixB bacteria in the feces during days 6-14 post-treatment (Table 1). Much of the increased diversity, however, was derived from commensal bacteria that were still present at low levels pre-treatment (Table 1), suggesting that the MixB bacteria had disrupted colonization by C. difficile 027/BI and the other members of the supershedder microbiota, triggering an expansion of the suppressed health-associated bacteria and a re-distribution of the microbiota to a healthy composition.

Cholate derivatives (i.e. Taurocholate and glycocholate) stimulate metabolically dormant spores to begin growth. Therefore addition of cholate-derivatives to the medium increases the chances of isolating such fastidious bacteria from the sample. This is how we identified one of the six MixB bacteria (Anaerostipes).

Significantly, and in contrast to the results with MixB, treatment of C. difficile 027/BI supershedder mice with further subdivisions of this bacterial mixture, including the MixB bacteria administered individually, or mixtures containing six or seven other cultured bacterial strains had a negligible impact on the supershedder state (FIG. 3b). To further illustrate the particular effectiveness of our MixB collection of strains, treatment of supershedders with a Bacteroides/Lactobacillus mixture, representative of more traditional probiotic bacterial groups (16, 17), failed to resolve the supershedder state and restore the recipients' microbiota to a healthy profile (FIG. 3a and FIG. 12). Thus, we rationally defined a novel, simple mixture consisting of six readily culturable intestinal bacterial strains that can cure C. difficile 027/BI infection in mice.

Figure 4:
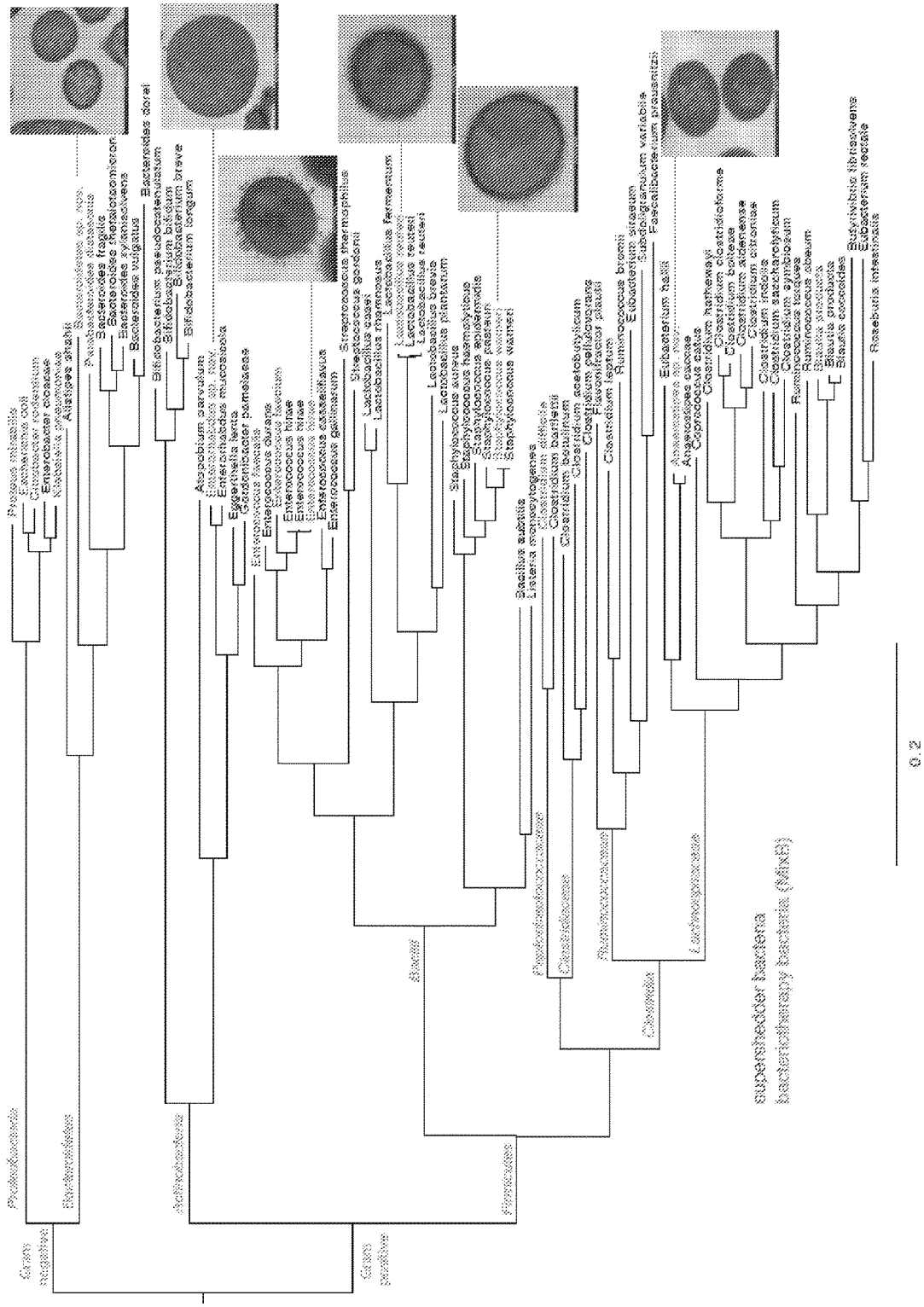
FIG. 4. Whole genome (Maximum likelihood) phylogeny of intestinal bacteria demonstrating the phylogenetic placement of protective bacteriotherapy bacteria (MixB) and the dominant members of the supershedder microbiota.

To gain insight into the genetic composition and fully define the identity of the six bacterial strains present in MixB (Table 2) we sequenced their genomes (and their closest equivalent human-derived species) and performed a phylogenetic comparison to reference intestinal bacterial genomes representative of the mammalian microbiota (FIG. 4 and Table 4). Based on this analysis we determined that MixB includes three previously described species, *Staphylococcus warneri*, *Enterococcus hirae*, *Lactobacillus reuteri*, and three novel species, *Anaerostipes* sp. nov., Bacteroidetes sp. nov. and *Enterorhabdus* sp. nov. (Table 2). This mix of bacteria is therefore phylogenetically diverse, including both obligate and facultative anaerobic species, and represents three of the four predominant intestinal microbiota phyla. Importantly, none of these species are known to be overtly pathogenic, they appear to be common inhabitants of the mouse intestine in health and they are phylogenetically distinct from the dominant members of the supershedder microbiota (FIG. 4). Given the demonstrated ineffectiveness of autoclaved feces, fecal filtrates, SFCAs and individual bacterial strains it therefore appears that displacement of *C. difficile* and the supershedder microbiota may require competition from a phylogenetically diverse and physiologically distinct collection of living bacteria.

In conclusion, we demonstrate that epidemic *C. difficile* 027/BI can out compete health-associated bacteria to enhance the contagious period of the host, increasing its likelihood of infecting a susceptible host. Restoration of a healthy microbiota with bacteriotherapy is viewed as a promising alternative treatment for recurrent *C. difficile* disease and other forms of intestinal dysbiosis (6, 14), but it is not widely used because of the time required to identify a suitable donor, the risk of introducing opportunistic pathogens as well as a general patient aversion (18). For the first time we demonstrate that it is also possible to eradicate *C. difficile* disease and contagiousness using a simple mixture of defined, culturable, components of the microbiota. Thus, our results open the way to rationally harness the therapeutic potential of health-associated microbial communities to treat recurrent *C. difficile* disease and transmission in humans, and potentially other forms of disease-associated dysbiosis.

FIG. 1. Epidemic *C. difficile* 027/BI Induces a Persisting Supershedder State with Enhanced Transmissibility Compared to Other Virulent Variants.

a) i-ii) hematoxylin and eosin staining to compare cecal pathology of i) healthy, clindamycin treated mice to ii) persistent *C. difficile* 027/BI-7 supershedders (day 49 post-infection; C57BL/6) that display signs of hyperplasia, edema and immune cell filtrate. Scale bars represent 100 μm. b) Representative fecal shedding patterns from C57BL/6 mice (n=5 mice per group) simultaneously treated with clindamycin and exposed to human virulent *C. difficile* spores to mimic natural transmission. Mice were infected with *C. difficile* ribotype 027 (strain BI-7; n=300), 017 (strain M68; n=240) and 012 (strain 630; n=50). Mice supershedding high-levels of *C. difficile* (>$10^8$ CFU/gram fresh feces) are highly contagious (i and iii) whereas mice shedding low-levels of *C. difficile* (ii; <$10^2$ CFU/gram fresh feces) are non-contagious. Broken horizontal line indicates culture detection limit. In the results in this figure, the top line in the graph which does not meet the broken horizontal line at any point represents *C. difficile* ribotype 027 results. The middle line which meets the broken horizontal line between day 25 and 30 on the X axis represents *C. difficile* ribotype 017 results. The line closest to the Y axis which meets the broken horizontal line around day 20 on the X axis represents *C. difficile* ribotype 012 results. c) *C. difficile* 027/BI-7 out competes *C. difficile* 012/R and 017/CF within susceptible host populations. Shown is the summary of two independent experiments where 3 infected donor mice were housed with 7 naïve recipient mice for 30 days in each experiment. The transmission rate of *C. difficile* 027/BI-7 is significantly different (p<1.1e-4) compared to that of *C. difficile* 012/630 (p<0.02) and 017/M68 (p<0.22).

FIG. 2. Fecal Bacteriotherapy Resolves Relapsing *C. difficile* 027/BI-7 Disease and Host Contagiousness.

a) *C. difficile* shedding patterns from mice (average from 5 mice/cage) demonstrating that *C. difficile* 027/BI infection is refractory to vancomycin treatment (van) and results in a relapsing supershedder state. Bacteriotherapy suppresses high-level *C. difficile* 027/BI-7 shedding (brown) whereas PBS administration had no impact on shedding levels (black). b) Supershedder mice efficiently transmit *C. difficile* to naïve mice whereas mice treated with feces and transformed to carriers become poor donors of infection to naive mice. Transmission efficiency refers to the percentage of naïve recipient mice (n=10/group) that became infected with *C. difficile* 027/BI-7. c) Quantitative RT-PCR of RNA extracted from supershedder mice cecal tissue showing high-level expression of the proinflammatory genes IL-6, iNOS and Ly6G, which were suppressed to levels comparable to naïve mice after bacteriotherapy. Cytokine expression was normalized to Gapdh and is shown as relative values.

FIG. 3. Effective Bacteriotherapy Re-Establishes a Healthy, Diverse Microbiota Profile in Epidemic *C. difficile* 027/BI Supershedder Mice.

a) Principal component analysis of the 16S rRNA gene sequences demonstrates that distinct microbiota profiles (circled) are associated with "healthy/naïve" mice, mice undergoing "clindamycin treatment" and "persisting supershedders" of *C. difficile* 027/BI-7. PC1 and PC2 account for 38% of the variation. Each symbol represents one microbiota (dot) or treatment (star) community. Treatment of supershedder mice with feces from healthy mice, the cultured fecal derivative or mixtures of defined, cultured bacteria are as indicated: brown—shading for healthy feces, blue—shading for fecal derivatives culture passaged once, green—shading for mixture of six suppressive bacteria (MixB) and grey—shading for *Bacteroides/Lactobacillus* mixture. The symbol representing the *Bacteroides/Lactobacillus* treatment is based on culturing counts and modified to reflect the relative abundance of each organism in the mixture. Next to the shading: pre=pre-treatment; 3=3 days post-treatment; 4=4 days post-treatment; 6=6 days post-treatment; 14=14 days post-treatment. Grey background arrows indicate the shifts in the microbiota profiles of treated mice over a 14-day period. b) Fecal shedding profiles from supershedder mice (n=5/group) that were treated with MixA, MixB or MixC (Table 2). In the results in this figure, the top line in the graph represents Mix C results; the middle line in the graph represents Mix A results; The line closest to the Y axis which meets the broken horizontal line around day 15 represents Mix B results. c) Shannon Diversity Indices of the intestinal microbiota of supershedders pre- and post-treatment (day 3, 6 and 14) with MixB and that of the corresponding input community.

FIG. 4. Whole Genome (Maximum Likelihood) Phylogeny of Intestinal Bacteria Demonstrating the Phylogenetic Placement of Protective Bacteriotherapy Bacteria (MixB) and the Dominant Members of the Supershedder Microbiota.

Maximum likelihood phylogeny produced using FastTree from the concatenated protein sequence of 44 common genes (See methods). Species names marked in green indicate members of the suppressive MixB mixture, names marked in red indicate species that were commonly detected in the feces of supershedding mice, names in black are reference genomes from common intestinal bacteria that were included to provide phylogenetic context to the tree. Taxonomic designations are given at the relevant branch nodes. Adjacent pictures are transmission electron micrographs of sectioned bacterial strains that constitute MixB. Methods for sample processing and imaging have been described (13). Scale bars are shown below bacteria.

REFERENCES

1. R. P. Vonberg et al., Infection control measures to limit the spread of *Clostridium difficile*. *Clinical microbiology and infection: the official publication of the European Society of Clinical Microbiology and Infectious Diseases* 14 Suppl 5, 2 (May, 2008).
2. D. N. Gerding, Clindamycin, cephalosporins, fluoroquinolones, and *Clostridium difficile*-associated diarrhea: this is an antimicrobial resistance problem. *Clinical infectious diseases: an official publication of the Infectious Diseases Society of America* 38, 646 (Mar. 1, 2004).
3. E. J. Kuipers, C. M. Surawicz, *Clostridium difficile* infection. *Lancet* 371, 1486 (May 3, 2008).
4. J. Y. Chang et al., Decreased diversity of the fecal microbiome in recurrent *Clostridium difficile*-associated diarrhea. *J Infect Dis* 197, 435 (Feb. 1, 2008).
5. C. J. Robinson, B. J. Bohannan, V. B. Young, From structure to function: the ecology of host-associated microbial communities. *Microbiol Mol Biol Rev* 74, 453 (September, 2010).
6. J. S. Bakken et al., Treating *Clostridium difficile* infection with fecal microbiota transplantation. *Clinical gastroenterology and hepatology: the official clinical practice journal of the American Gastroenterological Association* 9, 1044 (December, 2011).
7. A. C. Clements, R. J. Magalhaes, A. J. Tatem, D. L. Paterson, T. V. Riley, *Clostridium difficile* PCR ribotype 027: assessing the risks of further worldwide spread. *The Lancet infectious diseases* 10, 395 (June, 2010).
8. M. He et al., Evolutionary dynamics of *Clostridium difficile* over short and long time scales. *Proceedings of the National Academy of Sciences of the United States of America* 107, 7527 (Apr. 20, 2010).
9. M. Warny et al., Toxin production by an emerging strain of *Clostridium difficile* associated with outbreaks of severe disease in North America and Europe. *Lancet* 366, 1079 (Sep. 24-30, 2005).
10. V. G. Loo et al., A predominantly clonal multi-institutional outbreak of *Clostridium difficile*-associated diarrhea with high morbidity and mortality. *The New England journal of medicine* 353, 2442 (Dec. 8, 2005).
11. L. C. McDonald et al., An epidemic, toxin gene-variant strain of *Clostridium difficile*. *The New England journal of medicine* 353, 2433 (Dec. 8, 2005).
12. T. D. Lawley et al., Antibiotic treatment of *clostridium difficile* carrier mice triggers a supershedder state, spore-mediated transmission, and severe disease in immunocompromised hosts. *Infection and immunity* 77, 3661 (September, 2009).
13. T. D. Lawley et al., Proteomic and genomic characterization of highly infectious *Clostridium difficile* 630 spores. *Journal of bacteriology* 191, 5377 (September, 2009).
14. T. J. Borody et al., Bacteriotherapy using fecal flora: toying with human motions. *J Clin Gastroenterol* 38, 475 (July, 2004).
15. M. Tvede, J. Rask-Madsen, Bacteriotherapy for chronic relapsing *Clostridium difficile* diarrhoea in six patients. *Lancet* 1, 1156 (May 27, 1989).
16. S. K. Mazmanian, J. L. Round, D. L. Kasper, A microbial symbiosis factor prevents intestinal inflammatory disease. *Nature* 453, 620 (May 29, 2008).
17. O. Schreiber et al., *Lactobacillus reuteri* prevents colitis by reducing P-selectin-associated leukocyte- and platelet-endothelial cell interactions. *Am J Physiol Gastrointest Liver Physiol* 296, G534 (March, 2009).
18. R. Palmer, Fecal matters. *Nature medicine* 17, 150 (February, 2011).

Figure 5:
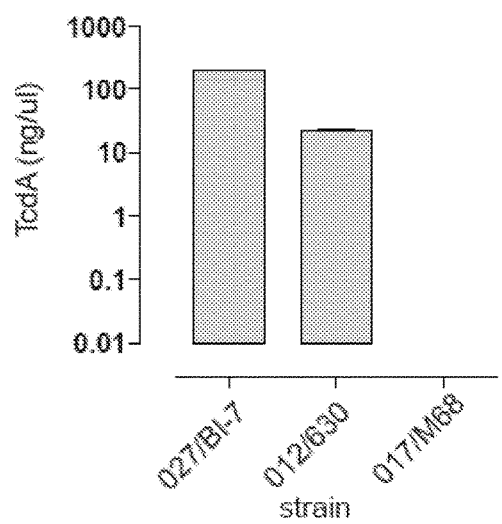
FIG. 5. Toxin A production by *C. difficile* 027/BI-7, 012/630 and 017/M68.

FIG. 5. Toxin A Production by *C. difficile* 027/BI-7, 012/630 and 017/M68.

*C. difficile* 027/BI produced TcdA at 200.3 ng/µl, *C. difficile* 630/012 produced TcdA at 21.5 ng/µl and *C. difficile* M68/017 does not produce TcdA. Data are from 3 independent experiments with triplicate determinants in each.

Figure 6:
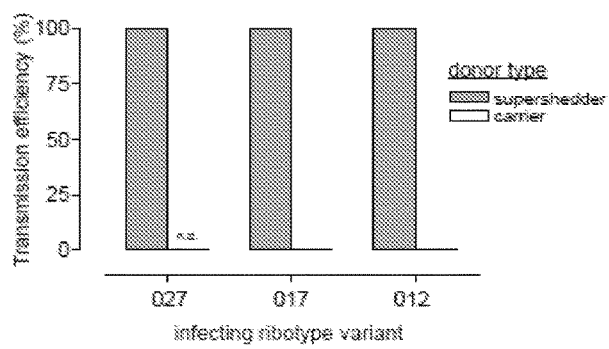
FIG. 6. *C. difficile* supershedders are highly contagious

FIG. 6. *C. difficile* supershedders are highly contagious.

Donor mice (from FIG. 1) infected with the indicated *C. difficile* variant were housed for 1 hour in sterile cages without bedding and then feces was removed and cages were left overnight so that only spore contamination remained. The next day naïve recipient mice were aseptically placed in cages for 1 hour and then aseptically removed and housed individually in sterile cages and given clindamycin in their drinking water. After 4 days the recipient mice were sampled to determine if they were infected with *C. difficile*. The transmission efficiency represents the percentage of recipient mice that became infected with *C. difficile*. Experiments were repeated at least twice and included 10 recipient mice per experiment. n.d=not determined FIG. 7 Epidemic *C. difficile* 027/BI-7 Induces Intestinal Dysbiosis in Mice.

a) Analysis of 16S rRNA gene sequences derived from feces of naïve mice (n=17), *C. difficile* carriers (n=5; 35-49 days post-infection), mice undergoing clindamycin treatment (n=12), mice recovered from clindmycin treatment (n=4; 42 days after cessation of treatment) and persisting supershedders of *C. difficile* 027/BI-7 (n=15; 35-49 days post-infection). SS=supershedder; car=carrier; clin recov=mice treated with clindamycin for 7 days and then sampled 42 days later; naïve clin=naïve mice treated with clindamycin for 7 days before sampling; 027 clin (017 clin)=mice infected with *C. difficile* 027/BI-7 (017/M68) and treated with clindamycin for 7 days before sampling. Mouse genotype (C57BL/6, C3H/HeN and C3H/HeJ) is also shown. b) Fecal short chain fatty acid profiles from naïve C57BL/6 mice, clindamycin-treated mice C57BL/6 mice that were not exposed to *C. difficile* 027/BI-7 and so their microbiota was allowed to recover and *C. difficile* 027/BI-7-supershedding C57BL/6 mice (n=5 mice/group).

FIG. 8 Impact of Various Oral Treatments on Epidemic *C. difficile* 027/BI Supershedder State in Mice.

Fecal shedding profile from supershedder mice (n=5/group) that were treated with feces or fecal derivatives. Standard treatments with a) feces and b) PBS are the same as in FIG. 2. The following treatments were administered into supershedder mice via oral gavage with a 200 µl volume. c) Equivalent feces was autoclaved using standard conditions and then resuspended in sterile PBS for a final concentration of 100 mg/ml. d) To produce fecal filtrate, feces was homogenized in sterile PBS at a concentration of 100 mg/ml and then centrifuged at 14,000 rpm for 10 minutes to separate the bacteria/particulate matter from the soluble fraction which was then filtered through a 0.22 μm filter. This was referred to as the fecal filtrate. e) SCFA indicates a mixture of acetate:propionate:butyrate in a ratio of 6:1:2 at a concentration of 100 mM that was at pH 6.5. f) Lab adapted *E. coli* strain C600 (nalidixic acid resistant) was gavaged into mice at a dose of $10^8$ CFU. *E. coli* colonization was confirmed by culturing feces of supershedder mice. The broken horizontal line indicates the detection limit.

FIG. 9 Distinct Intestinal Microbiota Community Structures from Healthy/Naïve Mice (n=17), Clindamycin Supershedders (*C. difficile* 027/BI-7 Infected Mice on Clindamycin; n=10) and Persisting Supershedders (*C. difficile* 027/BI-7 Infected Mice not on Clindamycin; n=17).

a) Plot illustrating the percentage of *C. difficile* 16S rRNA gene clones in libraries of healthy/naïve mice (n=4,926 clones), clindamycin supershedders (n=4,433 clones) and persisting supershedders (n=2,956 clones). b) Comparison of SDI for the intestinal microbiota of healthy/naïve mice, clindamycin supershedders and persisting supershedders. Wilcoxon rank sum test was used to compare differences between groups.

Figure 10:
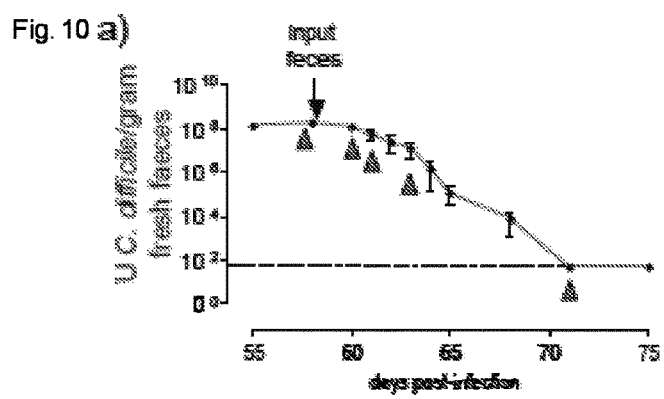
FIGS. 10A-C. Opportunistic pathogens routinely cultured from the feces of epidemic *C. difficile* 027/BI supershedder mice.
Figure 10:
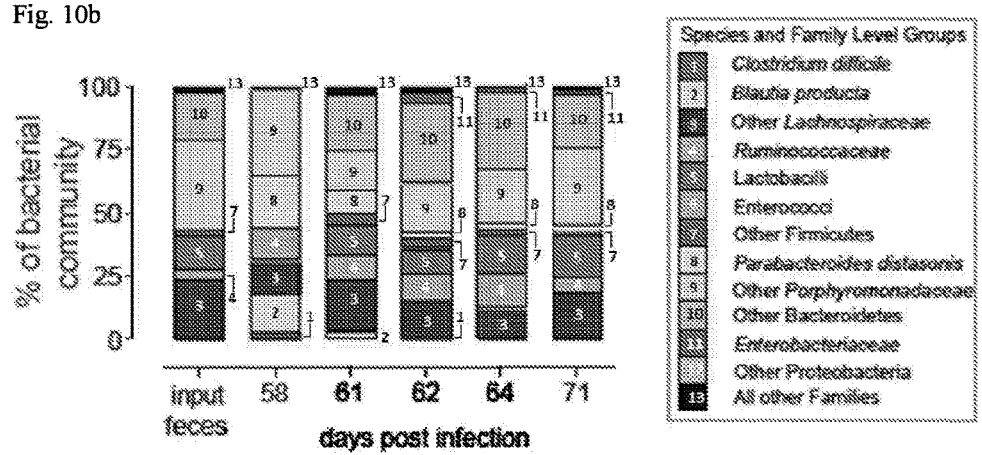
Figure 10C:
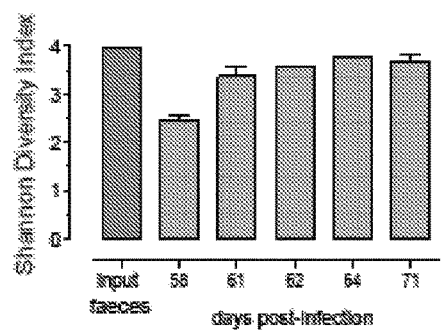

FIG. 10. Opportunistic Pathogens Routinely Cultured from the Feces of Epidemic *C. difficile* 027/BI Supershedder Mice.

Bacteria were identified as described in the Methods section and are shown here streaked onto a UTI diagnostic agar plate (Oxoid, Cambridge, UK).

FIG. 11. Fecal Bacteriotherapy Suppresses *C. difficile* Intestinal Colonization and Diversifies the Intestinal Bacterial Community of Supershedder Mice.

a) High-level excretion of *C. difficile* is rapidly suppressed after oral inoculation of supershedder mice with homogenized feces from a healthy mouse (input feces). Plotted red line represents average shedding levels of 5 mice and error bars indicate standard deviation. Black vertical arrow indicates day 58 when healthy feces was administered and green arrowheads indicate the times when fecal DNA was extracted for 16S rRNA gene analysis. b) Composition of intestinal bacterial community of supershedder mice (n=2) shifts to reflect that from the healthy donor mouse after bacteriotherapy. c) Diversity of intestinal microbiota of supershedder mice increases after bacteriotherapy as indicated by an increase in the Shannon Diversity Index scores.

FIG. 12. Simplified Fecal Derivatives Enriched for Easily Culturable Components Effectively Suppress the Epidemic *C. difficile* Supershedder 027/BI State in Mice.

a) Fecal shedding profiles from supershedder mice (n=5/group) that were treated with healthy feces, a *Bacteroides/Lactobacillus* mixture (*Bacteroides acidifaciens, Bacteroides vulgatus, Lactobacillus murinus* and *Lactobacillus reuteri*), feces cultured in Wilkins-Chalgren Anaerobic broth at 37° C. either aerobically or anaerobically. Pie charts illustrate the composition of the input treatments based on 16S rRNA gene clone libraries for healthy feces, aerobic passaged and anaerobic passaged inputs or based on culturing for the *Bacteroides/Lactobacillus* mixture. b) Shannon Diversity Indices of the intestinal microbiota of supershedders pre- and post-treatment (day 3, 4, 6 and 14) and that of the corresponding input community.

FIG. 13 Rarefaction Curves Demonstrating Observed Bacterial Diversity of Feces from Healthy, Naïve Mice and its Serially Passaged Derivatives.

In addition, the Chao1 calculator estimated the total community diversity (OTU defined at ≥98% similarity) for the healthy feces as 142 phylotypes (95% confidence interval 105-225), passage 1 as 30 phylotypes (95% confidence interval 27-46), passage 2 as 6 phylotypes (95% confidence interval 5-18) and passage 3 as 4 phylotypes (95% confidence interval 4-4). Together, these results demonstrate that serial passage of healthy feces in nutrient broth progressively reduced the complexity of the bacterial community.

Methods

Bacterial Culturing.

*C. difficile* strains BI-7 (genotype 027/BI; clindamycin[R], thiamphenicol[R], erythromycin[S]), M68 (genotype 017/CF; clindamycin[R], thiamphenicol[S], erythromycin[S]) and 630 (genotype 012/R; clindamycin[R], thiamphenicol[S], erythromycin[R]) have been described (1, 2). Culturing of *C. difficile* for infections and from feces was described previously (1). To isolate the intestinal bacteria from mouse feces or passaged fecal derivatives, the samples were serially diluted in sterile PBS, plated on a panel of nutrient agar plates; Luria Bertani, Brain Heart Infusion, Man Rogosa Sharpe, Fastidious anaerobic media, Columbia base media supplemented with 10% defribrinated horse blood, Wilkins-Chalgren anaerobic media (all media from Becton, Dickinson, Oxford, UK) and grown either aerobically or anaerobically at 37° C. for 24-72 hours. Distinct colony types were isolated, culture purified and genomic DNA was isolated to sequence the 16S rRNA gene using broad range primers as described in the microbiota section below. 16S rRNA gene sequences were compared to the GenBank and RDP databases to identify the bacterial species.

TcdA ELISA.

*C. difficile* cultures were grown in Wilson's broth (1) with shaking for 30 h, pelleted by centrifugation and supernatant was removed for TcdA quantification. Microtitre plates (96 well) were coated with capture antibody by adding 50 μl/well of a 2 μg/ml solution of anti-TcdA (TGCBiomics GmbH, Mainz, Germany) in PBS, and incubating overnight at 4° C. Plates were then washed three times in 0.05% Tween20 in PBS (PBS-T) and blocked with 200 μl 1% BSA (bovine serum albumin) in PBS for 2 h at room temperature. Purified TcdA from *C. difficile* strain VP110463 (TGCBiomics GmbH, Mainz, Germany) was diluted in 1% BSA-PBS (50 μl/well) and used to construct a standard curve. Culture filtrates were diluted as above in order to generate readings within the linear range of the standard curve. Plates were then incubated at room temperature for 2 h, followed by washing in PBS-T as above. The detection antibody (rabbit anti-*Clostridium difficile* toxin A; antibodies-online GmbH, Aachen, Germany) was diluted 1:5000 in 1% BSA-PBS, added to wells (50 μl/well) and incubated for 2 h at room temperature. After washing, polyclonal swine anti-rabbit IgG conjugated to horseradish peroxidase (Dako, Cambridgeshire, UK) was diluted 1:1000 in 1% BSA-PBS, added to the wells (50 μl/well) and incubated for 2 h at room temperature. Finally, plates were washed and 100 μl 3,3',5,5'-tetramethylbenzidine (TMB; Sigma Aldrich, Dorset, UK) substrate was added for 30 min at room temperature in the dark. 50 μl 0.5 M $H_2SO_4$ was added to stop the reaction. Absorbance was then measured at 450 nm on a FLUOStar Omega (BMG Labtech, Bucks, UK).

Mouse Infections.

Female mice between 5-9 weeks of age and from the genetic backgrounds C57BL/6, C57BL/6 p40$^{-/-}$, C3H/HeN and C3H/HeJ were routinely used. Mice to be used as *C. difficile* spore donors were infected with $10^5$ *C. difficile* cells via oral gavage and immediately clindamycin (250 mg/L; Apollo Scientific Ltd, Chesire, UK) was added to the drinking water for 1 week to induce high-level spore excretion. To infect experimental mice, one petri dish of contaminated bedding was removed from spore donor cages, placed into recipient mice cages and clindamycin (250 mg/L) was added to the drinking water for 1 week to induce the supershedder phenotype. To infect germ-free C3H/HeN mice, the feces of supershedder mice was collected, diluted in serial PBS and inoculated into mice via oral gavage. To suppress infection, vancomycin (300 mg/L; Sigma Aldrich, York, UK) was added to the drinking water for 10 days. To assess impact of infection, mice were sacrificed at indicated times and cecal tissue was aseptically collected and fixed for pathology as described (1), or fixed for RNA extractions by immersing samples in RNA-later (Applied Biosystems, Warrington, UK).

Bacteriotherapy Treatment.

To prepare input for bacteriotherapy, 1 gram of fresh feces was collected from 5 naïve mice, homogenized in 5 ml of sterile PBS and centrifuged for 30 seconds at 14,000 RPM to pellet the particulate matter. The supernatant slurry was collected and 200 µl was gavaged into each mouse within 30 minutes of excretion. To create the defined bacterial mixtures, individual bacteria were grown in Wilkins-Chalgren broth (*Lactobacillus* in Man Rogosa Sharpe broth) for 48-72 hours under anaerobic conditions at 37° C. Bacteria were harvested by centrifugation and re-suspending the pellet in 2 mls of sterile, pre-reduced PBS. Approximately $10^{10}$ of each bacterium was gavaged into each mouse in a 200 µl volume. To passage healthy feces, two fecal pellets (~50 mg) were collected aseptically and immediately placed into 20 ml of Wilkins-Chalgren Anaerobic broth or Luria broth that was pre-warmed to 37° C. under aerobic or anaerobic conditions. Fecal pellets were physically disrupted within the broth using a sterile pipette tip and subsequently incubated standing for 16 hours. For serial passage, 200 µl of the fecal derivative was inoculated into fresh broth and grown as described. For inoculations, the 20 ml cultures were pelleted and then resuspended into 2 ml of sterile PBS pre-warmed to 37° C. under aerobic or anaerobic conditions. Based on visual counts, approximately $4\times10^8$ (anaerobic passage) and $8\times10^8$ (aerobic passage) bacteria were gavaged into each mouse in a 200 µl volume.

Microarrays.

RNA purification from cecal mucosal tissue was performed using a Qiagen RNeasy mini kit (Qiagen, Austin, Tex., USA) according to the manufacturer's protocol. Quality control and quantification were performed using Bioanalyzer 2100 (Agilent Technologies, Palo Alto, Calif., USA) and Nanodrop ND100 (Nanodrop Technologies, Wilminton, Del.). RNA samples were then amplified and labelled using the Illumina TotalPrep 96 kit (Ambion, Austin, Tex., USA) and hybridized onto Illumina™ Mouse WG-6-V2 Beadchips (Illumina, San Diego, Calif., USA). The chips were scanned on an Illumina BeadArray Reader and raw intensities were extracted using Illumina BeadStudio Gene Expression Module.

Normalization and analysis of the microarrays were performed using GeneSpring X software (Agilent Technologies, Berkshire, UK). Normalization procedures utilized were quantile normalization and median of all samples baseline correction. For each comparison, differentially expressed genes were defined as having a fold change ≥2 and a FDR (false discovery rate) corrected p-value 0.05. Adjusted p-values were calculated using the Benjamini and Hochberg method (3).

RT-PCR.

Quantitative expression analysis was performed by real-time TaqMan RT-PCR on the ABI PRISM 7900HT Sequence Detection System (Applied Biosystems, Warrington, UK) as described previously (4). Expression of IL-6, iNOS and Ly6G was normalized to Gapdh mRNA. TaqMan primers and probes were designed to span exon junctions or to lie in different exons to prevent amplification of genomic DNA, as described (4). Primer and probe sequences are shown in Table 3. Probes were labelled with the reporter dye FAM at the 5'- and the quencher dye TAMRA at the 3'-end.

Transmission Experiments.

Protocols to test the contagiousness of infected donors (supershedders or carriers) have been described (1). To compare the contagiousness of different *C. difficile* strains mice infected with either *C. difficile* 012 (strain 630), 017 (strain M68) and 027 (strain BI-7) (immediately after cessation of 7 days of clindamycin treatment) were co-housed with 7 naïve recipient mice for 30 days. Experiments were repeated for a total of 14 naïve mice. To determine if recipient mice were infected with *C. difficile* they were individually placed (aseptically) in sterile cages for 3 days and given clindamycin in their drinking water for 4 days (1). Afterwards, feces was collected from individual mice and *C. difficile* enumerated by standard methods (1). Antibiotic resistance profiles were used to determine which *C. difficile* strain had infected mice.

Analysis of Microbiota.

Fecal DNA extraction, clone library construction and sequencing were carried out as described previously (1). Sequences were aligned using the RDP aligner (5) and these alignments were manually curated in the ARB package (6) before further analysis. Otherwise, sequences were checked and classified as described previously (7). In total 19,991 sequences were generated and these were deposited in GenBank (accession numbers JF241944-JF260864 and HE605382-HE608150).

The species diversity in each sample was measured by calculating the Shannon Diversity Index, which takes into account both species richness and relative proportional abundance (evenness), using the mothur software package (8). Rarefaction curves and Chao1 estimates of total bacterial diversity were also calculated in mothur (8).

Cluster dendrograms and PCA plots were based on a master alignment, which was built using the RDP aligner and subjected to manual curation. Using this alignment a distance matrix, with Felsenstein correction, was created using ARB. The distance matrix was then used as an input for DOTUR (9) using a 98% identity cut-off under the default furthest-neighbor setting. Sequences with >98% phylogenetic similarity were regarded as belonging to the same OTU. These OTUs were then used to calculate cluster dendrograms, using the Bray Curtis calculator, in the mothur package (8). 336 OTUs (12,308 clones) contributed to this analysis. Cluster dendrograms, with added bar charts showing the microbial composition of each sample and Shannon Diversity Indices, were visualized using the iTOL web package (10). For the PCA plot OTUs were generated as above but with a 97% identity cut-off. PCA decomposition was performed on the (symmetric) matrix of pairwise sample similarity, where the similarity metric was based on the sum of absolute differences in OTU frequency. 344 OTUs (16,154 clones) contributed to the analysis, which was insensitive to the removal of low frequency OTUs.

To determine the SCFA profile, the cecal contents from 5 mice per group were pooled and then resuspended in sterile PBS at a concentration of 500 mg/ml, homogenized and centrifuged at 14,000 rpm for 10 minutes. Supernatant was collected, acidified and following conversion to t-butyldimethylsilyl derivatives were analyzed by gas chromatography (11).

Whole Genome Sequencing and Phylogenetic Analysis of Intestinal Bacteria.

We sequenced the genomes (and their closest equivalent human-derived species) using the MiSeq platform, and performed de novo assembly using Velvet {(12) and gene prediction using GLIMMER3 (13). We then identified the genes that were in common between the 6 MixB species, and reference intestinal bacterial genomes sourced from the MetaHIT project, the HGMI project, and the Human Microbiome Project (Tables 4 and 5). 44 Common genes were identified using TBLASTN (14) searches against the complete dataset of the reference and assembled genomes for 80 bacteria (Table 5). Although the "true" core genome amongst these samples may be higher—we were limited by the fact that in several cases only draft assemblies were available, and so some genes which may have been expected to be present in the "core" group, were in fact not present, due to their absence in one or more of the draft genome sequences used. A gene was classified as being 'present' if it had a minimum percent amino acid identity across the entire gene of 30% compared to the reference. The reference genes used for querying were taken from the strain of *Staphylococcus warneri* taken from MixB. The common genes so identified were manually checked, translated, extracted, and concatenated together. We then used FastTree 2.1 (15), with its default settings (BLOSUM45 and the Jones-Taylor-Thorton CAT model, with 20 rate categories), to generate a maximum likelihood phylogeny from the concatenated protein sequence, in order to place the bacteria into their correct context and to distinguish species.

REFERENCES

1. T. D. Lawley et al., Antibiotic treatment of *clostridium difficile* carrier mice triggers a supershedder state, spore-mediated transmission, and severe disease in immunocompromised hosts. *Infection and immunity* 77, 3661 (September, 2009).
2. M. He et al., Evolutionary dynamics of *Clostridium difficile* over short and long time scales. *Proceedings of the National Academy of Sciences of the United States of America* 107, 7527 (Apr. 20, 2010).
3. Y. Hochberg, Y. Benjamini, More powerful procedures for multiple significance testing. *Stat Med* 9, 811 (July, 1990).
4. R. Rad et al., CD25+/Foxp3+ T cells regulate gastric inflammation and *Helicobacter pylori* colonization in vivo. *Gastroenterology* 131, 525 (2006).
5. J. R. Cole et al., The Ribosomal Database Project: improved alignments and new tools for rRNA analysis. *Nucleic Acids Res* 37, D141 (January, 2009).
6. W. Ludwig et al., ARB: a software environment for sequence data. *Nucleic Acids Res* 32, 1363 (2004).
7. A. W. Walker et al., Dominant and diet-responsive groups of bacteria within the human colonic microbiota. *The ISME journal* 5, 220 (Aug. 5, 2011).
8. P. D. Schloss et al., Introducing mothur: open-source, platform-independent, community-supported software for describing and comparing microbial communities. *Applied and environmental microbiology* 75, 7537 (December, 2009).
9. P. D. Schloss, J. Handelsman, Introducing DOTUR, a computer program for defining operational taxonomic units and estimating species richness. *Applied and environmental microbiology* 71, 1501 (March, 2005).
10. I. Letunic, P. Bork, Interactive Tree Of Life (iTOL): an online tool for phylogenetic tree display and annotation. *Bioinformatics* 23, 127 (Jan. 1, 2007).
11. A. J. Richardson, A. G. Calder, C. S. Stewart, A. Smith, Simultaneous determination of volatile and non-volatile acidic fermentation products of anaerobes by capillary gas chromatography. *Letters in applied microbiology* 9, 5 (1989).
12. D. R. Zerbino, E. Birney, Velvet: algorithms for de novo short read assembly using de Bruijn graphs. *Genome research* 18, 821 (May, 2008).
13. A. L. Delcher, K. A. Bratke, E. C. Powers, S. L. Salzberg, Identifying bacterial genes and endosymbiont DNA with Glimmer. *Bioinformatics* 23, 673 (Mar. 15, 2007).
14. J. Gertz, J. C. Fay, B. A. Cohen, Phylogeny based discovery of regulatory elements. *BMC bioinformatics* 7, 266 (2006).
15. M. N. Price, P. S. Dehal, A. P. Arkin, FastTree 2—approximately maximum-likelihood trees for large alignments. *PloS one* 5, e9490

TABLE 1

Summary of 16S rRNA gene clone library data used in this study.
19,991 sequences, generated from a total of 87 samples, were included in the study.
Bacteriotherapy suppresses the *Clostridium difficile* supershedder state
Phylum-Level Summary

| Info | Mouse Genotype | No. of clones | Shannon Diversity S.D.I. 99% | S.D.I. 98% | RDP Classification at Phylum Level (% of total clones) | | | | | | | GenBank/EMBL-Bank Accession Numbers |
|---|---|---|---|---|---|---|---|---|---|---|---|---|
| | | | | | Firmicutes | *C. difficile* | Bacteroidetes | Proteobacteria | Actinobacteria | Deferribacteres | Uncl. | |
| Naïve mouse d 0 | C57BL/6 | 231 | 4.14997 | 4.08776 | 63.2 | 0 | 33.3 | 0 | 0.9 | 2.6 | 0 | JF241944-JF242174 |
| M68 supershedder day 17 post-infection (17 days clindamycin) | C57BL/6 | 248 | 2.1051 | 2.1051 | 77.8 | 20.6 | 0 | 22.2 | 0 | 0 | 0 | JF242175-JF242422 |
| M68 supershedder day 20 post-infection | C57BL/6 | 213 | 2.18171 | 2.18171 | 74.2 | 22.1 | 0 | 25.8 | 0 | 0 | 0 | JF242423-JF242635 |
| M68 supershedder day 49 post-infection | C57BL/6 | 246 | 3.38848 | 3.24137 | 58.5 | 0 | 34.1 | 6.9 | 0.4 | 0 | 0 | JF242636-JF242881 |

TABLE 1-continued

Summary of 16S rRNA gene clone library data used in this study.
19,991 sequences, generated from a total of 87 samples, were included in the study.
Bacteriotherapy suppresses the *Clostridium difficile* supershedder state Phylum-Level Summary

| Info | Mouse Genotype | No. of clones | Shannon Diversity | | RDP Classification at Phylum Level (% of total clones) | | | | | | | GenBank/EMBL-Bank Accession Numbers |
|---|---|---|---|---|---|---|---|---|---|---|---|---|
| | | | S.D.I. 99% | S.D.I. 98% | Firmicutes | *C. difficile* | Bacter-oidetes | Proteo-bacteria | Actino-bacteria | Deferri-bacteres | Uncl. | |
| Naïve mouse d 0 | C57BL/6 | 227 | 4.21427 | 4.16541 | 64.3 | 0 | 35.2 | 0 | 0 | 0.4 | 0 | JF242882-JF243108 |
| M68 supershedder day 17 post-infection (17 days clindamycin) | C57BL/6 | 245 | 2.02013 | 2.02013 | 80.8 | 26.2 | 0 | 19.2 | 0 | 0 | 0 | JF243109-JF243353 |
| M68 supershedder day 20 post-infection | C57BL/6 | 236 | 2.25285 | 2.10025 | 77.5 | 17.8 | 0 | 22.5 | 0 | 0 | 0 | JF243354-JF243589 |
| M68 supershedder day 49 post-infection | C57BL/6 | 258 | 3.46856 | 3.25321 | 53.5 | 0 | 36 | 9.7 | 0.8 | 0 | 0 | JF243590-JF243847 |
| Naïve mouse d 0 | C57BL/6 | 244 | 3.91966 | 3.8975 | 52.9 | 0 | 45.5 | 0 | 0.4 | 1.2 | 0 | JF243848-JF244091 |
| M68 supershedder day 17 post-infection (17 days clindamycin) | C57BL/6 | 246 | 1.87254 | 1.77443 | 47.2 | 20.3 | 0.4 | 52.4 | 0 | 0 | 0 | JF244092-JF244337 |
| M68 supershedder day 20 post-infection | C57BL/6 | 253 | 2.30345 | 2.16097 | 71.9 | 26.5 | 0 | 28.1 | 0 | 0 | 0 | JF244338-JF244590 |
| M68 supershedder day 49 post-infection | C57BL/6 | 271 | 1.74011 | 1.65221 | 70.8 | 15.5 | 0 | 29.2 | 0 | 0 | 0 | JF244591-JF244861 |
| Naïve mouse d 0 | C57BL/6 | 231 | 3.79986 | 3.63532 | 51.5 | 0 | 47.6 | 0 | 0.9 | 0 | 0 | JF244862-JF245092 |
| M68 supershedder day 17 post-infection (17 days clindamycin) | C57BL/6 | 229 | 1.98981 | 1.98981 | 58.1 | 24.5 | 0 | 41.9 | 0 | 0 | 0 | JF245093-JF245321 |
| M68 supershedder day 20 post-infection | C57BL/6 | 223 | 2.07725 | 2.01554 | 73.5 | 39.9 | 0 | 26.5 | 0 | 0 | 0 | JF245322-JF245544 |
| M68 supershedder day 49 post-infection | C57BL/6 | 236 | 1.88852 | 1.8704 | 63.1 | 11.4 | 0 | 36.9 | 0 | 0 | 0 | JF245545-JF245780 |
| BI-7 supershedder 6 days post-bacteriotherapy (feces) | C57BL/6 | 228 | 3.56975 | 3.54283 | 37.3 | 0 | 57.9 | 3.5 | 0 | 0.9 | 0.4 | JF245781-JF246008 |
| BI-7 supershedder 6 days post-bacteriotherapy (feces) | C57BL/6 | 183 | 3.55612 | 3.55612 | 49.7 | 0 | 49.7 | 0 | 0 | 0 | 0.5 | JF246009-JF246191 |
| BI-7 supershedder 14 days post-bacteriotherapy (feces) | C57BL/6 | 198 | 3.82148 | 3.731 | 48 | 0 | 48.5 | 1.5 | 1.5 | 0.5 | 0 | JF246192-JF246389 |
| BI-7 supershedder 14 days post-bacteriotherapy (feces) | C57BL/6 | 236 | 3.51724 | 3.49493 | 37.3 | 0 | 59.3 | 1.7 | 0.4 | 0.8 | 0.4 | JF246390-JF246625 |

TABLE 1-continued

Summary of 16S rRNA gene clone library data used in this study.
19,991 sequences, generated from a total of 87 samples, were included in the study.
Bacteriotherapy suppresses the *Clostridium difficile* supershedder state
Phylum-Level Summary

| Info | Mouse Genotype | No. of clones | Shannon Diversity S.D.I. 99% | S.D.I. 98% | RDP Classification at Phylum Level (% of total clones) Firmicutes | *C. difficile* | Bacter-oidetes | Proteo-bacteria | Actino-bacteria | Deferri-bacteres | Uncl. | GenBank/ EMBL-Bank Accession Numbers |
|---|---|---|---|---|---|---|---|---|---|---|---|---|
| Naïve mouse - Day −2 | C57BL/6 | 234 | 3.19332 | 3.19332 | 57.3 | 0 | 39.7 | 2.1 | 0.9 | 0 | 0 | JF246626-JF246859 |
| Naïve mouse - Day 7 | C57BL/6 | 252 | 3.5617 | 3.51119 | 71 | 0 | 27 | 1.2 | 0.8 | 0 | 0 | JF246860-JF247111 |
| Naïve mouse - Day 49 | C57BL/6 | 241 | 3.33 | 3.33 | 58.5 | 0 | 40.2 | 0.4 | 0 | 0.8 | 0 | JF247112-JF247352 |
| Naïve mouse - Day −2 | C57BL/6 | 238 | 3.3436 | 3.3436 | 51.3 | 0 | 48.3 | 0 | 0.4 | 0 | 0 | JF247353-JF247590 |
| Naïve mouse - Day 7 | C57BL/6 | 263 | 3.58141 | 3.52961 | 46.4 | 0 | 49.8 | 1.5 | 2.3 | 0 | 0 | JF247591-JF247853 |
| Naïve mouse - Day 49 | C57BL/6 | 234 | 3.43067 | 3.43067 | 42.3 | 0 | 57.7 | 0 | 0 | 0 | 0 | JF247854-JF248087 |
| Naïve mouse - pre clindamycin | C57BL/6 | 231 | 3.81317 | 3.81317 | 63.2 | 0 | 33.3 | 2.2 | 0.9 | 0.4 | 0 | JF248088-JF248318 |
| Clindamycin treated - Day 7 | C57BL/6 | 256 | 2.03355 | 1.86828 | 77.3 | 0 | 0 | 22.7 | 0 | 0 | 0 | JF248319-JF248574 |
| Clindamycin treated - Day 49 | C57BL/6 | 229 | 3.74052 | 3.674 | 94.3 | 0 | 5.7 | 0 | 0 | 0 | 0 | JF248575-JF248803 |
| Naïve mouse - pre clindamycin | C57BL/6 | 249 | 2.93131 | 2.87491 | 50.2 | 0 | 49.8 | 0 | 0 | 0 | 0 | JF248804-JF249052 |
| Clindamycin treated - Day 7 | C57BL/6 | 228 | 1.56548 | 1.56548 | 53.9 | 0 | 0 | 46.1 | 0 | 0 | 0 | JF249053-JF249280 |
| Clindamycin treated - Day 49 | C57BL/6 | 222 | 3.63564 | 3.5173 | 90.1 | 0 | 8.6 | 0.9 | 0.5 | 0 | 0 | JF249281-JF249502 |
| Naïve mouse - pre clindamycin/ *C. diff* | C57BL/6 | 227 | 3.4708 | 3.4708 | 43.2 | 0 | 56.4 | 0 | 0.4 | 0 | 0 | JF249503-JF249729 |
| BI-7 supershedder day 7 post-infection | C57BL/6 | 246 | 1.40816 | 1.04058 | 34.1 | 31.7 | 0 | 65.9 | 0 | 0 | 0 | JF249730-JF249975 |
| BI-7 supershedder day 49 post-infection | C57BL/6 | 251 | 1.59185 | 1.59185 | 50.6 | 12 | 46.6 | 2.8 | 0 | 0 | 0 | JF249976-JF250226 |
| Naïve mouse - pre clindamycin/ *C. diff* | C57BL/6 | 192 | 3.51133 | 3.44958 | 39.6 | 0 | 59.4 | 1 | 0 | 0 | 0 | JF250227-JF250418 |
| BI-7 supershedder day 7 post-infection | C57BL/6 | 257 | 1.29546 | 1.29546 | 54.5 | 35 | 0 | 45.5 | 0 | 0 | 0 | JF250419-JF250675 |
| BI-7 supershedder day 49 post-infection | C57BL/6 | 229 | 2.03132 | 1.8842 | 30.6 | 4.4 | 64.2 | 5.2 | 0 | 0 | 0 | JF250676-JF250904 |
| BI-7 supershedder day 49 post-infection | C3H/HeN | 231 | 1.94559 | 1.52807 | 42 | 1.3 | 55 | 3 | 0 | 0 | 0 | JF250905-JF251135 |
| BI-7 supershedder day 49 post-infection | C3H/HeN | 246 | 1.77284 | 1.36087 | 36.2 | 0.4 | 61 | 2.8 | 0 | 0 | 0 | JF251136-JF251381 |
| Clindamycin treated 7 days and recovered 42 days - Day 49 | C3H/HeN | 233 | 4.03206 | 3.93299 | 73.8 | 0 | 26.2 | 0 | 0 | 0 | 0 | JF251382-JF251614 |
| Clindamycin treated 7 days and recovered 42 days - Day 49 | C3H/HeN | 232 | 3.52201 | 3.44376 | 55.6 | 0 | 44.4 | 0 | 0 | 0 | 0 | JF251615-JF251846 |
| Naïve mouse - Day 49 | C3H/HeN | 240 | 3.72625 | 3.71829 | 50 | 0 | 49.2 | 0.4 | 0 | 0.4 | 0 | JF251847-JF252086 |
| Naïve mouse - Day 49 | C3H/HeN | 221 | 3.38237 | 3.38237 | 24.4 | 0 | 69.7 | 0 | 0 | 5.9 | 0 | JF252087-JF252307 |

TABLE 1-continued

Summary of 16S rRNA gene clone library data used in this study.
19,991 sequences, generated from a total of 87 samples, were included in the study.
Bacteriotherapy suppresses the *Clostridium difficile* supershedder state Phylum-Level Summary

| Info | Mouse Genotype | No. of clones | Shannon Diversity | | RDP Classification at Phylum Level (% of total clones) | | | | | | | GenBank/EMBL-Bank Accession Numbers |
|---|---|---|---|---|---|---|---|---|---|---|---|---|
| | | | S.D.I. 99% | S.D.I. 98% | Firmicutes | *C. difficile* | Bacteroidetes | Proteobacteria | Actinobacteria | Deferribacteres | Uncl. | |
| Feces from healthy donor mouse/source of cultured fecal samples | C57BL/6 | 240 | 3.68282 | 3.65063 | 37.1 | 0 | 62.1 | 0 | 0.8 | 0 | 0 | JF252308-JF252547 |
| Aerobic culture of sample 16sms225 | C57BL/6 | 219 | 2.77561 | 2.44051 | 54.8 | 0 | 29.7 | 15.1 | 0.5 | 0 | 0 | JF252548-JF252766 |
| BI-7 supershedder pre-bacteriotherapy (aerobic culture) | C57BL/6 | 238 | 2.31896 | 2.31896 | 87.4 | 13.45 | 0 | 12.6 | 0 | 0 | 0 | JF254466-JF254703 |
| BI-7 supershedder 6 days post-bacteriotherapy (aerobic culture) | C57BL/6 | 232 | 3.24385 | 3.04048 | 26.3 | 0 | 68.5 | 3.9 | 1.3 | 0 | 0 | JF254704-JF254935 |
| BI-7 supershedder 14 days post-bacteriotherapy (aerobic culture) | C57BL/6 | 238 | 3.36589 | 3.20486 | 30.7 | 0 | 66.8 | 2.1 | 0.4 | 0 | 0 | JF254936-JF255173 |
| BI-7 supershedder pre-bacteriotherapy (aerobic culture) | C57BL/6 | 215 | 2.33625 | 2.30886 | 75.8 | 20.93 | 24.2 | 0 | 0 | 0 | 0 | JF255174-JF255388 |
| BI-7 supershedder 6 days post-bacteriotherapy (aerobic culture) | C57BL/6 | 238 | 3.13471 | 3.00441 | 16.4 | 0 | 80.7 | 2.5 | 0.4 | 0 | 0 | JF255389-JF255626 |
| BI-7 supershedder 14 days post-bacteriotherapy (aerobic culture) | C57BL/6 | 236 | 3.07781 | 2.93903 | 35.2 | 0 | 61 | 3.8 | 0 | 0 | 0 | JF255627-JF255862 |
| BI-7 supershedder pre-bacteriotherapy (Bac/Lac mix) | C57BL/6 | 250 | 1.62768 | 1.62768 | 83.2 | 14 | 0 | 16.8 | 0 | 0 | 0 | JF255863-JF256112 |
| BI-7 supershedder 6 days post-bacteriotherapy (Bac/Lac mix) | C57BL/6 | 216 | 1.62933 | 1.6085 | 35.2 | 3.7 | 58.3 | 6.5 | 0 | 0 | 0 | JF256113-JF256328 |
| BI-7 supershedder 14 days post-bacteriotherapy (Bac/Lac mix) | C57BL/6 | 211 | 1.79599 | 1.78694 | 31.3 | 0.5 | 66.8 | 1.9 | 0 | 0 | 0 | JF256329-JF256539 |
| Supershedder pre-bacteriotherapy (Bac/Lac mix) | C57BL/6 | 210 | 1.84808 | 1.80343 | 77.6 | 15.2 | 0 | 22.4 | 0 | 0 | 0 | JF256540-JF256749 |
| BI-7 supershedder 6 days post-bacteriotherapy (Bac/Lac mix) | C57BL/6 | 235 | 1.60486 | 1.60486 | 50.2 | 3.4 | 48.1 | 1.7 | 0 | 0 | 0 | JF256750-JF256984 |
| BI-7 supershedder 14 days post-bacteriotherapy (Bac/Lac mix) | C57BL/6 | 237 | 1.9682 | 1.9682 | 40.5 | 1.7 | 57.8 | 1.7 | 0 | 0 | 0 | JF256985-JF257221 |

TABLE 1-continued

Summary of 16S rRNA gene clone library data used in this study.
19,991 sequences, generated from a total of 87 samples, were included in the study.
Bacteriotherapy suppresses the *Clostridium difficile* supershedder state Phylum-Level Summary

| Info | Mouse Genotype | No. of clones | Shannon Diversity S.D.I. 99% | S.D.I. 98% | RDP Classification at Phylum Level (% of total clones) |||||| | GenBank/EMBL-Bank Accession Numbers |
|---|---|---|---|---|---|---|---|---|---|---|---|---|
| | | | | | Firmicutes | *C. difficile* | Bacteroidetes | Proteobacteria | Actinobacteria | Deferribacteres | Uncl. | |
| BI-7 supershedder day 49 post-infection | C3J/HeJ | 78 | 1.43267 | 1.43267 | 52.6 | 16.7 | 42.3 | 5.1 | 0 | 0 | 0 | JF257222-JF257299 |
| BI-7 supershedder day 49 post-infection | C3H/HeJ | 88 | 1.96344 | 1.49214 | 34.1 | 9.1 | 50 | 15.9 | 0 | 0 | 0 | JF257300-JF257387 |
| BI-7 supershedder day 49 post-infection | C3H/HeN | 252 | 1.98776 | 1.70844 | 57.1 | 9.5 | 39.7 | 3.2 | 0 | 0 | 0 | JF257388-JF257639 |
| BI-7 supershedder day 49 post-infection | C57BL/6 | 258 | 2.58617 | 2.23557 | 40.7 | 4.7 | 57.4 | 1.9 | 0 | 0 | 0 | JF257640-JF257897 |
| BI-7 carrier day 49 post-infection | C57BL/6 | 231 | 3.29611 | 3.27958 | 73.2 | 0 | 26.4 | 0.4 | 0 | 0 | 0 | JF257898-JF258128 |
| BI-7 carrier day 49 post-infection | C57BL/6 | 213 | 3.24006 | 3.20816 | 54.5 | 0 | 45.5 | 0 | 0 | 0 | 0 | JF258129-JF258341 |
| BI-7 carrier day 49 post-infection | C57BL/6 | 209 | 3.15434 | 3.13857 | 57.4 | 0 | 42.6 | 0 | 0 | 0 | 0 | JF258342-JF258550 |
| BI-7 supershedder day 49 post-infection | C57BL/6 | 223 | 2.15049 | 1.6202 | 46.6 | 4 | 52.9 | 0.4 | 0 | 0 | 0 | JF258551-JF258773 |
| BI-7 supershedder day 49 post-infection | C57BL/6 p40−/− | 224 | 1.65811 | 1.65811 | 45.5 | 4.5 | 51.3 | 3.1 | 0 | 0 | 0 | JF258774-JF258997 |
| BI-7 supershedder day 49 post-infection | C57BL/6 p40−/− | 301 | 2.19324 | 1.98225 | 36.9 | 2.7 | 62.1 | 1 | 0 | 0 | 0 | JF258998-JF259298 |
| Input Feces for bacteriotherapy | C57BL/6 | 223 | 3.93654 | 3.8962 | 43.5 | 0 | 53.8 | 0.4 | 0 | 1.8 | 0.4 | JF259299-JF259521 |
| BI-7 supershedder pre-bacteriotherapy (feces) | C57BL/6 | 244 | 2.50776 | 2.31929 | 46.7 | 3.3 | 52 | 1.2 | 0 | 0 | 0 | JF259522-JF259765 |
| BI-7 supershedder pre-bacteriotherapy (feces) | C57BL/6 | 245 | 2.41999 | 2.12256 | 42.4 | 2.4 | 56.7 | 0.8 | 0 | 0 | 0 | JF259766-JF260010 |
| BI-7 supershedder 3 days post-bacteriotherapy (feces) | C57BL/6 | 242 | 3.15804 | 3.11079 | 49.6 | 0.4 | 47.5 | 1.7 | 0 | 0.8 | 0.4 | JF260011-JF260252 |
| BI-7 supershedder 3 days post-bacteriotherapy (feces) | C57BL/6 | 211 | 3.55141 | 3.54236 | 49.8 | 0 | 46 | 0 | 0 | 3.3 | 0.9 | JF260253-JF260463 |
| BI-7 supershedder 4 days post-bacteriotherapy (feces) | C57BL/6 | 207 | 3.77395 | 3.76309 | 38.6 | 0 | 51.7 | 6.8 | 0.5 | 0.5 | 1.9 | JF260464-JF260670 |
| BI-7 supershedder 4 days post-bacteriotherapy (feces) | C57BL/6 | 194 | 3.72324 | 3.72324 | 41.8 | 0 | 53.6 | 2.1 | 0 | 1 | 1.5 | JF260671-JF260864 |

TABLE 1-continued

Summary of 16S rRNA gene clone library data used in this study.
19,991 sequences, generated from a total of 87 samples, were included in the study.
Bacteriotherapy suppresses the *Clostridium difficile* supershedder state
Phylum-Level Summary

| Info | Mouse Genotype | No. of clones | Shannon Diversity S.D.I. 99% | S.D.I. 98% | RDP Classification at Phylum Level (% of total clones) Firmicutes | *C. difficile* | Bacter-oidetes | Proteo-bacteria | Actino-bacteria | Deferri-bacteres | Uncl. | GenBank/ EMBL-Bank Accession Numbers |
|---|---|---|---|---|---|---|---|---|---|---|---|---|
| SS - after two courses of Vancomycin | C57BL/6 | 203 | 1.99917 | 1.99917 | 90.1 | 16.7 | 0 | 9.9 | 0 | 0 | 0 | HE605382-HE605584 |
| SS - persisting for months | C57BL/6 | 210 | 1.71892 | 1.70296 | 39 | 4.3 | 56.2 | 4.8 | 0 | 0 | 0 | HE605585-HE605794 |
| SS - after two courses of Vancomycin | C57BL/6 | 210 | 1.82721 | 1.82721 | 92.4 | 7.6 | 0 | 7.6 | 0 | 0 | 0 | HE605795-HE606004 |
| Supershedder (Prior to Mix B treatment) | C57BL/6 | 239 | 2.74342 | 2.74342 | 47.3 | 0.42 | 51 | 1.7 | 0 | 0 | 0 | HE606005-HE606243 |
| Supershedder (Prior to Mix B Treatment) | C57BL/6 | 210 | 2.64761 | 2.64761 | 58.6 | 1.43 | 41 | 0.5 | 0 | 0 | 0 | HE606244-HE606453 |
| TL90_Mix B Bacteriotherapy Input | C57BL/6 | 237 | 1.46435 | 1.46435 | 94.1 | 0 | 3.4 | 0 | 2.5 | 0 | 0 | HE606454-HE606690 |
| Supershedder 4 days post bacteriotherapy (Mix B) | C57BL/6 | 261 | 2.74376 | 2.74376 | 43.3 | 0.38 | 53.6 | 2.7 | 0.4 | 0 | 0 | HE606691-HE606951 |
| Supershedder 4 days post bacteriotherapy (Mix B) | C57BL/6 | 242 | 2.8643 | 2.8643 | 52.1 | 0 | 46.7 | 1.2 | 0 | 0 | 0 | HE606952-HE607193 |
| Supershedder 6 days post bacteriotherapy (Mix B) | C57BL/6 | 259 | 3.1317 | 3.1317 | 52.5 | 0 | 45.2 | 2.3 | 0 | 0 | 0 | HE607194-HE607452 |
| Supershedder 6 days post bacteriotherapy (Mix B) | C57BL/6 | 244 | 3.10992 | 3.09076 | 57.8 | 0.41 | 41.4 | 0.8 | 0 | 0 | 0 | HE607453-HE607696 |
| Supershedder 14 days post bacteriotherapy (Mix B) | C57BL/6 | 235 | 3.03497 | 3.03497 | 45.1 | 0 | 52.8 | 1.3 | 0.9 | 0 | 0 | HE607697-HE607931 |
| Supershedder 14 days post bacteriotherapy (Mix B) | C57BL/6 | 219 | 3.26271 | 3.21437 | 57.5 | 0 | 42 | 0.5 | 0 | 0 | 0 | HE607932-HE608150 |

TABLE 2

Bacterial species isolated from cultured fecal derivative.
Species designation is based on the sequence of the 16S rRNA gene or Whole Genome
Sequencing and comparative genomic using the genomes of intestinal bacteria.

| Mix | Species based on 16S rRNA gene | Genus Species based on WGS | Phylum |
|---|---|---|---|
| A | *Bacteroides acidifaciens* | | Bacteroidetes |
| A | 16saw22-1a06.p1k, *Barnesiella intestinihominis* (87%) | | Bacteroidetes |
| A | *Lactobacillus taiwanensis/gasseri/johnsonii* | | Firmicutes |
| A | *Flavonifractor plautii* | | Firmicutes |
| A | R-7912, *Turicibacter sanguinis* (97%) | | Firmicutes |
| A | *Bifidobacterium pseudolongum* subsp. *globosum/pseudolongum* | | Actinobacteria |
| A | *Escherichia coli* | | Proteobacteria |
| B | 16saw22-1a06.p1k, *Barnesiella intestinihominis* (87%) | Bacteroidetes novel species | Bacteroidetes |
| B | *Lactobacillus reuteri* | *Lactobacillus reuteri* | Firmicutes |
| B | *Enterococcus hirae/faecium/durans* | *Enterococcus hirae* | Firmicutes |
| B | *Anaerostipes caccae/Clostridium indolis* | Anaerostipes novel species | Firmicutes |

TABLE 2-continued

Bacterial species isolated from cultured fecal derivative.
Species designation is based on the sequence of the 16S rRNA gene or Whole Genome
Sequencing and comparative genomic using the genomes of intestinal bacteria.

| Mix | Species based on 16S rRNA gene | Genus Species based on WGS | Phylum |
|---|---|---|---|
| B | Staphlococcus warneri/pasteuri | Staphlococcus warneri | Firmicutes |
| B | WD3_aako2b03 Adlercreutzia equolifaciens (97%) | Enterorhabdus novel species | Actinobacteria |
| C | Parabacteroides distasonis | | Bacteroidetes |
| C | 16saw22-1a06.p1k, Barnesiella intestinihominis (87%) | | Bacteroidetes |
| C | Lactobacillus murinus/animalis | | Firmicutes |
| C | Enterococcus faecalis | | Firmicutes |
| C | Blautia producta | | Firmicutes |
| C | Propionibacterium acnes | | Actinobacteria |
| C | Acinetobacter lwoffii/baumannii | | Proteobacteria |
| B1 | WD3-aako2b03, Adlercreutsia equolifaciens (97%) | Enterorhabdus novel species | Actinobacteria |
| B1 | Anaerostipes caccae/Clostridium indolis | Anaerostipes novel species | Firmicutes |
| B1 | Staphlococcus warneri/pasteuri | Staphlococcus warneri | Firmicutes |
| B2 | 16saw22-1a06.p1k, Barnesiella intestinihominis (87%) | Bacteroidetes novel species | Bacteroidetes |
| B2 | Lactobacillus reuteri | Lactobacillus reuteri | Firmicutes |
| B2 | Enterococcus hirae/faecium/durans | Enterococcus hirae | Firmicutes |

TABLE 3

Primers used for RT-PCR experiments shown in FIG. 3.

| Primer name | Sequence |
|---|---|
| Gapdh F | 5'-TGTGTCCGTCGTGGATCTGA-3' (SEQ ID No.: 1) |
| Gapdh R | 5'-CACCACCTTCTTGATGTCATCATAC-3' (SEQ ID No.: 2) |
| Gapdh probe* | 5'-TGCCGCCTGGAGAAACCTGCC-3' (SEQ ID No.: 3) |
| IL-6 F | 5'-ACAAGTCGGAGGCTTAATTACACAT-3' (SEQ ID No.: 4) |
| IL-6 R | 5'-TTGCCATTGCACAACTCTTTTC-3' (SEQ ID No.: 5) |
| IL-6 probe* | 5'-TTCTCTGGGAAATCGTGGAAATG-3' (SEQ ID No.: 6) |
| iNOS F | 5'-TGCATCGGCAGGATCCA-3' (SEQ ID No.: 7) |
| iNOS R | 5'-AACATTTCCTGTGCTGTGCTACA-3' (SEQ ID No.: 8) |
| iNOS probe* | 5'-CCTGCAGGTCTTTGACGCTCGGAA-3' (SEQ ID No.: 9) |
| Ly6G F | 5'-TGCCCCTTCTCTGATGGATT-3' (SEQ ID No.: 10) |
| Ly6G R | 5'-TGCTCTTGACTITGCTICTGTGA-3' (SEQ ID No.: 11) |
| Ly6G probe* | 5'- TGCGTTGCTCTGGAGATAGAAGTTAT TGTGGACT-3' (SEQ ID No.: 12) |

*Probes were labeled with FAM (5') and TAMRA (3').

TABLE 4

Summary of data used whole genome phylogeny of intestinal bacteria presented in FIG. 4.

| Species | Accession Number/link |
|---|---|
| Proteus mirabilis | am942759 |
| Escherichia coli | cp000802 |
| Citrobacter rodentium | fn543502 |
| Enterobacter cloacae | FP929040 |
| Klebsiella pneumoniae | ERS012055 |
| Alistipes shahii | FP929032 |
| Bacteroidetes sp. nov. | ERS084472 |
| Parabacteroides distasonis | cp000140 |
| Bacteroides fragilis | fq312004 |
| Bacteroides thetaiotaomicron | ae015928 |
| Bacteroides xylanisolvens | FP929033 |
| Bacteroides vulgatus | cp000139 |
| Bacteroides dorei | ftp://ftp.sanger.ac.uk/pub/pathogens/Bacteroides/dorei/D8/improved/Bacteroides_dorei_D8.fasta |
| Bifidobacterium pseudocatenulatum | ftp://ftp.sanger.ac.uk/pub/pathogens/Bifidobacterium/pseudocatenulatum/D2CA/improved/Bifidobacterium_pseudocatenulatum_D2CA.fasta |
| Bifidobacterium bifidum | cp001840 |
| Bifidobacterium breve | cp000303 |
| Bifidobacterium longum | cp000605 |
| Atopobium parvulum | cp001721 |
| Enterorhabdus sp. nov. | ERS084471 |
| Enterorhabdus mucosicola | ERS084484 |
| Eggerthella lenta | cp001726 |
| Gordonibacter pamelaeae | FP929047 |
| Bacillus subtilis | CM000488 |
| Staphylococcus aureus | FN433596 |
| Staphylococcus haemolyticus | AP006716 |
| Staphylococcus epidermidis | CP000029 |
| Staphylococcus pasteuri | ERS084477 |
| Staphylococcus warneri | ERS084483 |
| Staphylococcus warneri | ERS084478 |
| Listeria monocytogenes | CP001604 |
| Lactobacillus casei | CP000423 |
| Lactobacillus rhamnosus | FM179323 |
| Lactobacillus fermentum | CP002033 |
| Lactobacillus reuteri | ERS084469 |
| Lactobacillus reuteri | ERS084476 |
| Lactobacillus reuteri | AP007281 |
| Lactobacillus brevis | CP000416 |
| Lactobacillus plantarum | CP002222 |

TABLE 4-continued

Summary of data used whole genome phylogeny of intestinal bacteria presented in FIG. 4.

| Species | Accession Number/link |
|---|---|
| Streptococcus thermophilus | CP000023 |
| Streptococcus gordonii | CP000725 |
| Enterococcus faecalis | CP002491 |
| Enterococcus durans | ERS084475 |
| Enterococcus faecium | GG692468-GG692536 |
| Enterococcus hirae | ERS084482 |
| Enterococcus hirae | ERS084473 |
| Enterococcus hirae | ERS084474 |
| Enterococcus casseliflavus | ACAH00000000 |
| Enterococcus gallinarum | ACAJ00000000 |
| Clostridium difficile | FN545816 |
| Clostridium bartletti | ABEZ00000000 |
| Clostridium botulinum | CP000962 |
| Clostridium cellulovorans | CP002160 |
| Clostridium acetobutylicum | ae001437 |
| Flavonifractor plautii | SRS084527 |
| Clostridium leptum | ABCB00000000 |
| Ruminococcus bromii | FP929051 |
| Eubacterium siraeum | FP929044 |
| Subdoligranulum variabile | SRS010483 |
| Faecalibacterium prausnitzii | FP929045 |
| Eubacterium hallii | ftp://ftp.sanger.ac.uk/pub/pathogens/Eubacterium/hallii/SM61/improved/Eubacterium_hallii_SM61.fasta |
| Coprococcus catus | FP929038 |
| Anerostipes sp. nov. | ERS084470 |
| Anaerostipes caccae | SRS211904 |
| Clostridium hathewayi | SRP006092 |
| Clostridium clostridioforme | SRP002711 |
| Clostridium bolteae | SRP002709 |
| Clostridium aldenense | SRP002708 |
| Clostridium citroniae | SRP003300 |
| Clostridium indolis | ERS084479 |
| Clostridium saccharolyticum | FP929037 |
| Clostridium synnbiosum | SRP003488 |
| Rumninococcus obeum | FP929054 |
| Blautia producta | |
| Blautia producta | |
| Blautia coccoides | ERS084481 |
| Ruminococcus torques | FP929055 |
| Butyrivibrio fibrisolvens | FP929036 |
| Eubacterium rectale | FP929042 |
| Roseburia intestinalis | FP929049 |

TABLE 5

Genes selected

| Gene |
|---|
| 30S ribosomal protein S1 |
| 30S ribosomal protein S10 |
| 30S ribosomal protein S13 |
| 30S ribosomal protein S14 type Z |
| 30S ribosomal protein S16 |
| 30S ribosomal protein S17 |
| 30S ribosomal protein S19 |
| 30S ribosomal protein S3 |
| 30S ribosomal protein S5 |
| 30S ribosomal protein S7 |
| 30S ribosomal protein S8 |
| 50S ribosomal protein L1 |
| 50S ribosomal protein L11 |
| 50S ribosomal protein L14 |
| 50S ribosomal protein L15 |
| 50S ribosomal protein L16 |
| 50S ribosomal protein L18P |
| 50S ribosomal protein L2 |
| 50S ribosomal protein L22 |
| 50S ribosomal protein L24 |
| 50S ribosomal protein L34 |
| 50S ribosomal protein L5 |
| 50S ribosomal protein L7/L12 |
| adenylate kinase |
| adenylosuccinate synthetase |
| bacterial peptide chain release factor 2 |
| D-methionine ABC transporter, ATP-binding protein |
| DNA gyrase subunit B |
| DNA primase |
| Excinuclease ABC subunit B |
| glutamine transport ATP-binding protein GlnQ |
| GMP synthase |
| heat shock protein GrpE |
| Holliday junction DNA helicase RuvA |
| KDP operon transcriptional regulatory protein KdpE |
| L-cystine import ATP-binding protein TcyC |
| methenyltetrahydrofolate cyclohydrolase |
| phenylalanyl-tRNA synthetase, alpha subunit |
| polyribonucleotide nucleotidyltransferase |
| Protein Translation Elongation Factor Ts (EF-Ts) |
| transcription termination/antitermination factor NusG |
| translation initiation factor IF-1 |
| Triosephosphate isomerase |
| YmdA/YtgF family protein |

The invention claimed is:

1. A method for the identification of bacterial species suitable for use in bacteriotherapy, the method comprising:
   (i) preparing a suspension of material collected from a host harbouring microbiota;
   (ii) adding an activator of bacterial spores sufficient to allow growth of bacteria from spores present in the suspension;
   (iii) culturing the suspension;
   (iv) detecting at least one bacterial species or a group of individual bacterial species within the suspension culture of step (iii) by genomic DNA sequencing, and; obtaining or isolating the at least one or group of detected individual bacterial species from the suspension culture;
   (v) assessing combinations of the isolated detected individual species from step (iv) to identify combinations of no more than 9 of the isolated detected individual bacterial species for use in, or suitable for use in, bacteriotherapy by:
      (a) administering the combinations of the isolated detected individual bacterial species assessed in step (vi) to a human or non-human animal recipient and measuring a shift in the recipient's microbiota to that of a healthy microbiota, wherein an increase in species diversity indicates a shift to healthy microbiota, and/or
      (b) assessing the combinations of the isolated detected individual bacterial species assessed in step (vi) in an animal model to identify combinations that are able to resolve a pathology in vivo by altering resident intestinal microbiota composition; and
   (vi) selecting a combination of no more than 9 of the isolated detected individual bacterial species assessed in step (v) that shifts the recipient's microbiota to that of a healthy microbiota by increasing species diversity, and/or resolves a pathology in vivo, for use in bacteriotherapy.

2. The method of claim 1 wherein the activator comprises a cholate derivative.

3. The method of claim 2, wherein the activator comprises taurocholate and/or glycocholate.

4. The method of claim 1 comprising the step of culturing the material under aerobic or anaerobic conditions.

5. The method of claim 1 further comprising a step of incubation of the suspension in a standing culture under aerobic or anaerobic conditions.

6. The method of claim 1, wherein the material collected from a host is fecal material or material obtained by biopsy or sampling from the gut of the host.

7. The method of claim 6 wherein the fecal material is from the intended recipient of bacteriotherapy prior to the need for bacteriotherapy or from a healthy donor.

8. The method of claim 1, wherein the material being cultured in step (iii) is first or second passage of a fecal sample from the host.

9. The method of claim 1, wherein the bacterial species suitable for use in bacteriotherapy comprises a spore forming bacteria.

10. The method of claim 1, wherein the method includes delivering the combination of no more than 9 of the detected individual bacterial species identified in step vii of claim 1 to a human or nonhuman animal to provide bacteriotherapy.

11. The method of claim 10, wherein the bacteriotherapy is for the treatment or prevention of recurrent diarrhoea; colitis; pseudomembranous colitis; ulcerative colitis; pouchitis; Antibiotic induced diarrhoea; viral infection; obesity; inflammatory bowel disease; Crohn's disease; irritable bowel syndrome; or a *C. difficile* syndrome.

12. The method of claim 1, wherein identification of at least one bacterial species or a group of individual bacterial species within the culture in step (iv) is by sequencing specific genes.

13. The method of claim 1, wherein identification of at least one bacterial species or a group of individual bacterial species within the culture in step (iv) is by sequencing its 16S rRNA genes.

14. The method of claim 1, wherein identification of at least one bacterial species or a group of individual bacterial species within the culture in step (iv) is by whole genome sequencing.

15. A method for the identification of bacterial species suitable for use in bacteriotherapy, the method comprising:
(i) preparing a culture of material collected from a host harbouring microbiota comprising an activator of bacterial spores sufficient to allow growth of bacteria from spores present in the culture;
(ii) detecting at least one bacterial species or a group of individual bacterial species within the culture of step (i) by genomic DNA sequencing, and
isolating the at least one or group of detected individual bacterial species from the culture;
(iii) assessing combinations of the isolated detected individual species from step (ii) to identify combinations of no more than 9 of the detected individual bacterial species for use in, or suitable for use in, bacteriotherapy by:
  (a) administering the combinations of the isolated detected individual bacterial species to a human or non-human animal recipient and measuring a shift in the recipient's microbiota to that of a healthy microbiota, wherein an increase in species diversity indicates a shift to healthy microbiota, and/or
  (b) assessing the combinations of the isolated detected individual bacterial species in an animal model to identify combinations that are able to resolve a pathology in vivo by altering resident intestinal microbiota composition; and
(iv) selecting a combination of no more than 9 of the isolated detected individual bacterial species assessed in step (iii) that shifts the recipient's microbiota to that of a healthy microbiota by increasing species diversity, and/or resolves a pathology in vivo, for use in bacteriotherapy.

* * * * *

UNITED STATES PATENT AND TRADEMARK OFFICE
CERTIFICATE OF CORRECTION

PATENT NO. : 10,130,665 B2
APPLICATION NO. : 14/402033
DATED : November 20, 2018
INVENTOR(S) : Lawley et al.

Page 1 of 1

It is certified that error appears in the above-identified patent and that said Letters Patent is hereby corrected as shown below:

In the Claims

At Claim 1, Column 54, Line 46, please replace "(vi ) to a human or non - human animal recipient and" with -- (v) to a human or non-human animal recipient and --.

At Claim 1, Column 54, Line 52, please replace "individual bacterial species assessed in step ( vi ) in an" with -- individual bacterial species assessed in step (v) in an --.

At Claim 10, Column 55, Line 17, please replace "individual bacterial species identified in step vii of claim 1" with -- individual bacterial species identified in step (vii) of claim 1 --.

Signed and Sealed this
Fourteenth Day of May, 2019

Andrei Iancu
*Director of the United States Patent and Trademark Office*